United States Patent
Lawton et al.

(10) Patent No.: US 11,327,067 B2
(45) Date of Patent: May 10, 2022

(54) RIVET MEASUREMENT SYSTEM

(71) Applicant: The Boeing Company, Chicago, IL (US)

(72) Inventors: Robert Michael Lawton, Huntsville, AL (US); Kelsea Cox, Harvest, AL (US); Lindsay Leigh Waite Jones, Madison, AL (US); Ivan V. Kwok, Mill Creek, WA (US)

(73) Assignee: The Boeing Company, Chicago, IL (US)

( * ) Notice: Subject to any disclaimer, the term of this patent is extended or adjusted under 35 U.S.C. 154(b) by 1388 days.

(21) Appl. No.: 15/602,735

(22) Filed: May 23, 2017

(65) Prior Publication Data

US 2018/0341725 A1  Nov. 29, 2018

(51) Int. Cl.
*G01N 33/20* (2019.01)
*G06F 30/20* (2020.01)
*G01N 33/00* (2006.01)
*G06F 111/10* (2020.01)

(52) U.S. Cl.
CPC ............ *G01N 33/20* (2013.01); *G06F 30/20* (2020.01); *G01N 2033/0083* (2013.01); *G06F 2111/10* (2020.01)

(58) Field of Classification Search
CPC .................................................... G01N 33/20
See application file for complete search history.

(56) References Cited

U.S. PATENT DOCUMENTS

| 4,823,396 | A | * | 4/1989 | Thompson | ............... B07C 5/10 |
| | | | | | 382/152 |
| 2018/0038836 | A1 | * | 2/2018 | Senderos | ............... G01N 29/50 |

* cited by examiner

*Primary Examiner* — John E Breene
*Assistant Examiner* — Jeffrey C Morgan
(74) *Attorney, Agent, or Firm* — Yee & Associates, P.C.

(57) ABSTRACT

A method, system, and apparatus for a rivet measurement system for non-destructive testing measurements comprising a first measurement apparatus, a second measurement apparatus and a rivet analyzer. The first measurement apparatus acquires non-destructive testing measurements for sample production grade rivets of a particular class installed in a production vehicle structure. The second measurement apparatus acquires destructive testing measurements for the sample production grade rivets of the particular class. The rivet analyzer creates a statistical model representing a relationship between the non-destructive testing measurements and destructive testing measurements of the production grade rivets and to acquire the non-destructive testing measurements for the button height and the button diameter for additional production grade rivets, predict rivet button concentricity from the non-destructive testing measurements for the button height and the button diameter using the statistical model and determine whether the additional production grade rivets installed in the production vehicle structure are acceptable.

23 Claims, 13 Drawing Sheets

| | 702 | 704 | 706 | 708 | 710 |
|---|---|---|---|---|---|
| | FASTENERS TYPE | FLUSHNESS | MeanButtonDiameter | ButtonHeight | CONCENTRICITY |
| | FV8KE8 | 0.0048 | 0.4125 | 0.102 | 0.075 |
| | FV8KE8 | 0.0051 | 0.4170 | 0.096 | 0.074 |
| 712 | FV8KE8 | 0.0047 | 0.4290 | 0.099 | 0.085 |
| | FV8KE8 | 0.0030 | 0.3925 | 0.090 | 0.060 |
| | FV8KE8 | 0.0032 | 0.3905 | 0.089 | 0.060 |
| | FV8KE8 | 0.0034 | 0.3930 | 0.090 | 0.062 |
| | FV8KE8 | 0.0033 | 0.3930 | 0.090 | 0.067 |
| | FV8KE8 | 0.0039 | 0.3915 | 0.089 | 0.063 |
| | FV8KE8 | 0.0037 | 0.3945 | 0.090 | 0.064 |
| | FV8KE8 | 0.0035 | 0.4075 | 0.088 | 0.078 |

| | 802 | 804 | 806 | 808 | 810 |
|---|---|---|---|---|---|
| | TERM | ESTIMATE | std.error | STATISTIC | p.value |
| 1 | (INTERCEPT) | 0.33909 | 0.13081 | 2.592 | 0.01087* |
| 2 | FastenerFV8KE8 | -0.00521 | 0.00306 | -1.706 | 0.09086 |
| 3 | MACHINE PROCESS | -0.01926 | 0.00093 | -20.674 | 0*** |
| 4 | MeanButtonDiameter | -0.65136 | 0.33499 | -1.944 | 0.05447 |
| 5 | ButtonHeight | -4.45744 | 1.42615 | -3.126 | 0.00229** |
| 6 | MeanButtonDiameter:ButtonHeight | 10.96679 | 3.62984 | 3.021 | 0.00315** |

RIVET MEASUREMENT SYSTEM

BACKGROUND INFORMATION

1. Field

The present disclosure relates generally to manufacturing vehicles, and in particular, to installing fasteners in manufacturing vehicles using a fastener measurement system.

2. Background

In manufacturing vehicles, fasteners are installed to connect parts to each other. For example, hundreds of thousands or millions of rivets may be installed in a commercial aircraft. Inspection of the installed rivets is performed to determine whether the rivets meet specifications for the commercial aircraft.

The inspection may be performed in a number different ways. The inspections may be performed using non-destructive testing and destructive testing.

Non-destructive testing may be performed by having human operators make measurements with tools, such as gauges or probes. Additionally, non-destructive testing may be performed using robots that have an end effector configured to make measurements. Measurements of rivets also may be obtained using cameras or laser measurement tools.

Some measurements, however, may not be easily made using human operators or robots with gauges, probes, cameras, or laser measurement tools. For example, some parameters cannot be viewed on installed rivets. One parameter of interest is rivet concentricity. This parameter is measured by drilling out the rivet and making measurements of the uninstalled rivet.

As a result, destructive testing may be employed to obtain measurements for rivet concentricity and other parameters. With destructive testing, the disassembly and removal of rivets to make measurements is often more time consuming and more costly than desired. Another drawback with destructive testing, however, is that an additional step occurs in which the rivet is reinstalled in the structure in the aircraft. This situation also increases the cost for manufacturing the commercial aircraft.

Therefore, it would be desirable to have a method and apparatus that take into account at least some of the issues discussed above, as well as other possible issues. For example, it would be desirable to have a method and apparatus that overcome a technical problem with obtaining measurements of desired parameters without using destructive testing.

SUMMARY

An embodiment of the present disclosure provides a rivet measurement system for non-destructive testing measurements of production rivets for a production vehicle structure. The rivet measurement system comprises a first measurement apparatus, a second measurement apparatus and a rivet analyzer. The first measurement apparatus is configured to acquire the non-destructive testing measurements for sample production grade rivets of a particular class installed in the production vehicle structure. The non-destructive testing measurements include a button height and a button diameter. The second measurement apparatus is configured to acquire destructive testing measurements for the sample production grade rivets of the particular class. The sample production grade rivets are drilled out and removed and the destructive testing measurements include a rivet button concentricity. The rivet analyzer is configured to create a statistical model representing a relationship between the non-destructive testing measurements and the destructive testing measurements of the production grade rivets. The rivet analyzer is further configured to acquire the non-destructive testing measurements for the button height and the button diameter for additional production grade rivets of the particular class installed in the production vehicle structure. The rivet analyzer predicts the rivet button concentricity for the additional production grade rivets from the non-destructive testing measurements for the button height and the button diameter using the statistical model. The rivet analyzer determines whether the additional production grade rivets installed in the production vehicle structure are acceptable by comparing the rivet button concentricity predicted for the production rivets to specification limits for the particular class, to thereby enable a comparison of the non-destructive testing measurements of the additional production grade rivets to the specification limits without having to perform destructive testing.

Another embodiment of the present disclosure provides a method for non-destructive testing measurements of production rivets for a production vehicle structure. The method acquires sample non-destructive testing measurements for sample production grade rivets of a particular class installed in the production vehicle structure for a production vehicle. The non-destructive testing measurements include a button height and a button diameter. The method acquires sample destructive testing measurements for the sample production grade rivets of the particular class. The sample production grade rivets are drilled out and removed and the sample destructive testing measurements include a rivet button concentricity. The method creates a statistical model representing a relationship between the sample non-destructive testing measurements and the sample destructive testing measurements of the sample production grade rivets. The method then acquires non-destructive testing measurements for the button height and the button diameter for the sample production grade rivets of the particular class installed in the production vehicle structure. The method predicts the rivet button concentricity for the sample production grade rivets from the non-destructive testing measurements for the button height and the button diameter using the statistical model. Finally, the method determines whether the sample production grade rivets installed in the production vehicle structure are acceptable by comparing the rivet button concentricity predicted for the sample production grade rivets to specification limits for the particular class, to thereby enable a comparison of non-destructive testing measurements of the sample production grade rivets to the specification limits without having to perform destructive testing.

Yet another embodiment of the present disclosure provides a method for non-destructive testing of production grade fasteners. The method acquires non-destructive testing measurements for the production grade fasteners of a particular class installed in a production vehicle structure. The method predicts destructive testing measurements for the production grade fasteners from the non-destructive testing measurements using a statistical model representing a relationship between the non-destructive testing measurements and the destructive testing measurements of the production grade fasteners. Finally, the method determines whether the production grade fasteners installed in the production vehicle structure are acceptable by comparing the destructive testing measurements predicted for the production grade fasteners to specification limits for the particular class, to thereby enable a comparison of the non-destructive testing measurements of additional production grade fasteners to the specification limits without having to perform destructive testing.

Another embodiment of the present disclosure provides a fastener measurement system for non-destructive testing measurements of production grade fasteners for a production vehicle structure. The fastener measurement system comprises an analyzer configured to acquire the non-destructive testing measurements for production grade fasteners of a particular class installed in the production vehicle structure. The analyzer predicts destructive testing measurements for the production grade fasteners from the non-destructive testing measurements using a statistical model representing a relationship between the non-destructive testing measurements and the destructive testing measurements of the production grade fasteners. The analyzer determines whether the production grade fasteners installed in the production vehicle structure are acceptable by comparing the destructive testing measurements predicted for the production grade fasteners to specification limits for the particular class, to thereby enable a comparison of the non-destructive testing measurements of additional production grade fasteners to the specification limits without having to perform destructive testing.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account one or more different considerations. For example, the illustrative embodiments recognize and take into account that it would be desirable to perform measurements without destructive testing. The illustrative embodiments recognize and take into account one type of non-destructive testing that may be used to identify a rivet parameter, such as concentricity, is the use of an x-ray system.

The illustrative embodiments recognize and take into account, however, that an x-ray system is a less desirable non-destructive testing system. An x-ray system may require removal or disassembly of parts to perform x-ray measurements. After an image is generated, the parts are reinstalled or reassembled. In other cases, the removal or disassembly of parts may not be needed but the cost of the equipment, specialized training for operators, and time-consuming steps for x-ray measurements make this type of technique undesirable. Thus, the illustrative embodiments recognize and take into account that an x-ray system is a less desirable non-destructive testing system because of the increase in time and effort needed to make measurements. The illustrative embodiments recognize that this type of system may increase the time and effort needed by great amounts when millions of rivets may be present.

Thus, the illustrative embodiments provide a method and apparatus for non-destructive testing of fasteners. A faster measurement system may be employed to perform non-destructive testing measurements of production grade fasteners for a production vehicle structure. In one illustrative example, non-destructive testing measurements for the production grade fasteners of a particular class are installed in a production vehicle structure. Destructive measurement values are predicted for the production grade fasteners from the non-destructive testing measurements using a statistical model that represents a relationship between the non-destructive testing measurements and the destructive testing measurements of the production grade fasteners. A determination is made as to whether the production grade fasteners installed in the production vehicle structure are acceptable by comparing the destructive testing values predicted for the production grade fasteners to specification limits for the particular class, to thereby enable a comparison of the non-destructive testing measurements of additional production grade fasteners to the specification limits without having to perform destructive testing.

Figure 1:
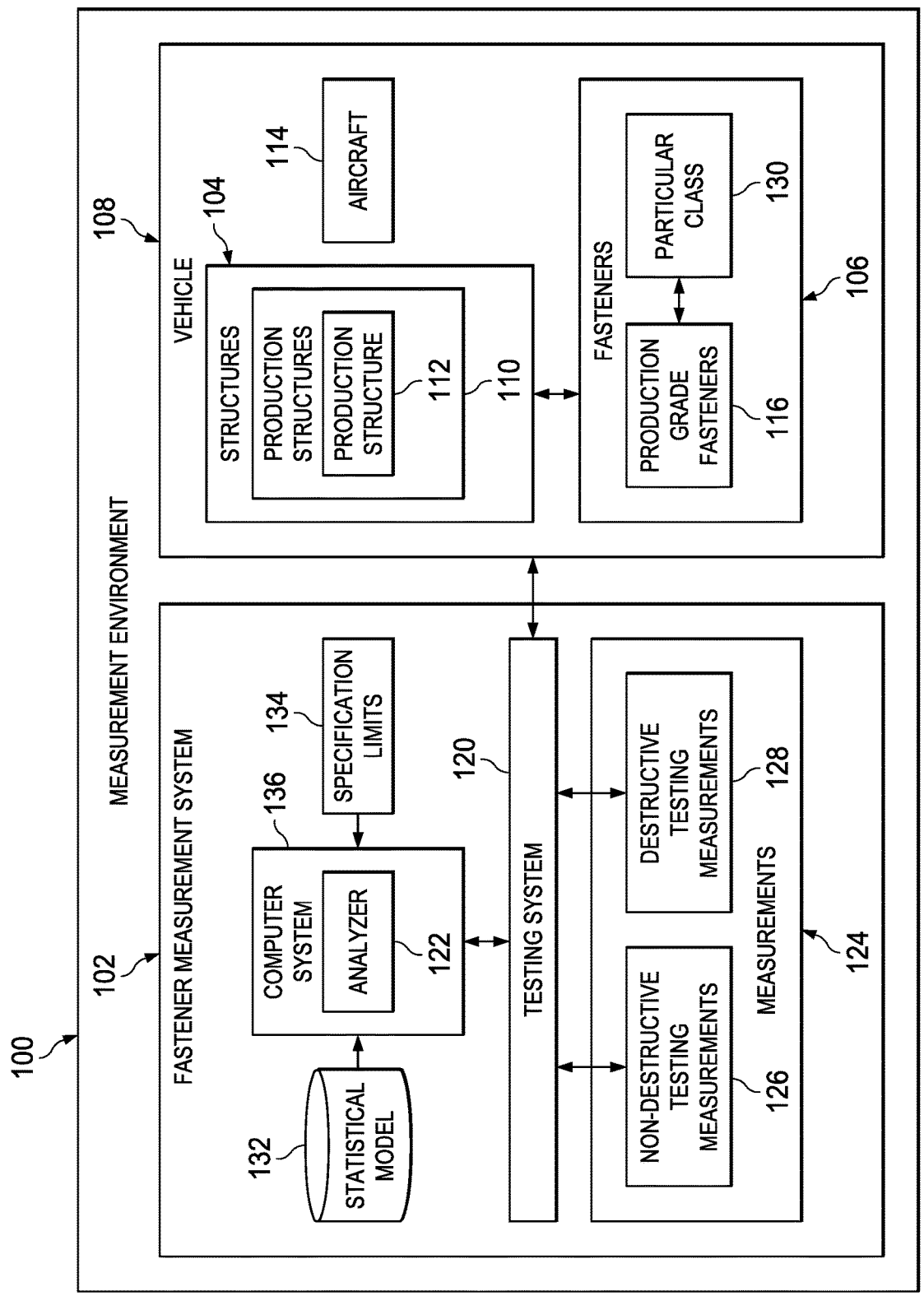
FIG. 1 is an illustration of a block diagram of a measurement environment in accordance with an illustrative embodiment.

With reference now to the figures and in particular with reference to FIG. 1, an illustration of a block diagram of a measurement environment is depicted in accordance with an illustrative embodiment. In this illustrative example, measurement environment 100 includes fastener measurement system 102. Fastener measurement system 102 is employed to make measurements of fasteners 106 used with structures 104 for vehicle 108. In these illustrative examples, structures 104 may take the form of production structures 110.

Structures 104 and production structures 110 may take different forms. For example, the structures may be selected from at least one of a skin panel, a conduit, a monument, an engine, an engine housing, a fuselage section, a wing box, a spar, a rib, a line replaceable unit (LRU), an electrical assembly, and other types of structures that may be used in vehicle 108. In this illustrative example, structures 104 and production structures 110 may be formed from one or more parts or components that are connected to each other using fasteners 106. In some illustrative examples, structures 104 and production structures 110 may only be formed from a single part that includes fasteners 106.

As depicted, production structure 112 is a structure that meets specifications for use in vehicle 108. Production structure 112 is a structure manufactured for testing or actual use in a production form of vehicle 108. For example, production structures 110 may meet one or more certification standards for vehicle 108 in the form of aircraft 114.

In these illustrative examples, fasteners 106 may be production grade fasteners 116. Production grade fasteners 116 are fasteners that meet specifications for use with structures 104. These specifications are used in certifying aircraft 114. The specifications may include at least one of geometries, materials, or other parameters.

As used herein, the phrase "at least one of", when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, without limitation, "at least one of item A, item B, or item C" may include item A, item A and item B, or item C. This example also may include item A, item B, and item C; or item B and item C. Of course, any combinations of these items may be present. In some illustrative examples, "at least one of" may be, for example, without limitation, two of item A, one of item B, and ten of item C; four of item B and seven of item C; or other suitable combinations.

Fastener measurement system 102 may be employed for non-destructive measurements of production grade fasteners 116 for production structure 112. Fastener measurement system 102 includes testing system 120 and analyzer 122.

In this illustrative example, testing system 120 includes one or more apparatuses that may be used to make measurements 124. Measurements 124 include at least one of non-destructive testing measurements 126 or destructive testing measurements 128. The apparatus in testing system 120 may include at least one of a gauge, a probe, a robot, a laser measurement unit, a camera, or some other suitable type of apparatus.

As depicted, analyzer 122 is configured to acquire non-destructive testing measurements 126 for fasteners 106 of particular class 130 installed in production structure 112. Analyzer 122 is also configured to predict destructive testing measurements 128 for production grade fasteners 116 from non-destructive testing measurements 126 using statistical model 132 that represents a relationship between non-destructive testing measurements 126 and destructive testing measurements 128 of production grade fasteners 116.

Further, statistical model 132 may take into account environmental factors. For example, environmental factors may include a particular fastening machine, a particular team of human operators, or other suitable factors. Environmental factors also may include machine process parameters, for example, an installation process, hammering time, force exertion settings, drill speed, and other parameters. These parameters may impact installations of fasteners 106. Examples of environmental factors may include process parameters such as material type, coating, and drill bit wear. Additional environmental factors include temperature, humidity, machine location, and other types of environmental factors.

Analyzer 122 is configured to determine whether production grade fasteners 116 installed in production structure 112 are acceptable by comparing destructive testing measurements 128 predicted for production grade fasteners 116 to specification limits 134 for particular class 130. In this manner, non-destructive testing measurements 126 of additional production grade fasteners to specification limits 134 is enabled without having to perform destructive testing.

As depicted, analyzer 122 may be located in computer system 136. Computer system 136 is a physical hardware system and includes one or more data processing systems. When more than one data processing system is present, those data processing systems are in communication with each other using a communications medium. The communications medium may be a network. The data processing systems may be selected from at least one of a computer, a server computer, a tablet, or some other suitable data processing system.

In the illustrative examples, analyzer 122 may be implemented in software, hardware, firmware, or a combination thereof. When software is used, the operations performed by analyzer 122 may be implemented in program code configured to run on hardware, such as a processor unit. When firmware is used, the operations performed by analyzer 122 may be implemented in program code and data, and stored in persistent memory to run on a processor unit. When hardware is employed, the hardware may include circuits that operate to perform the operations in analyzer 122.

In the illustrative examples, the hardware may take a form selected from at least one of a circuit system, an integrated circuit, an application specific integrated circuit (ASIC), a programmable logic device, or some other suitable type of hardware configured to perform a number of operations. With a programmable logic device, the device may be configured to perform a number of operations. The device may be reconfigured at a later time or may be permanently configured to perform the number of operations. Programmable logic devices include, for example, a programmable logic array, a programmable array logic, a field programmable logic array, a field programmable gate array, and other suitable hardware devices. Additionally, the processes may be implemented in organic components integrated with inorganic components and may be comprised entirely of organic components. For example, the processes may be implemented as circuits in organic semiconductors.

In one illustrative example, one or more technical solutions are present that overcome a technical problem with obtaining measurements of desired parameters without using destructive testing. As a result, one or more technical solutions may provide a technical effect to identifying destructive testing measurements without having to perform destructive testing. One or more technical solutions are present that provide an ability to predict destructive testing measurements using statistical models.

As a result, computer system 136 operates as a special purpose computer system in which analyzer 122 in computer system 136 enables predicting destructive testing measurements 128 from non-destructive testing measurements 126. In particular, analyzer 122 transforms computer system 136 into a special purpose computer system, as compared to currently available general computer systems that do not have analyzer 122.

Figure 2:
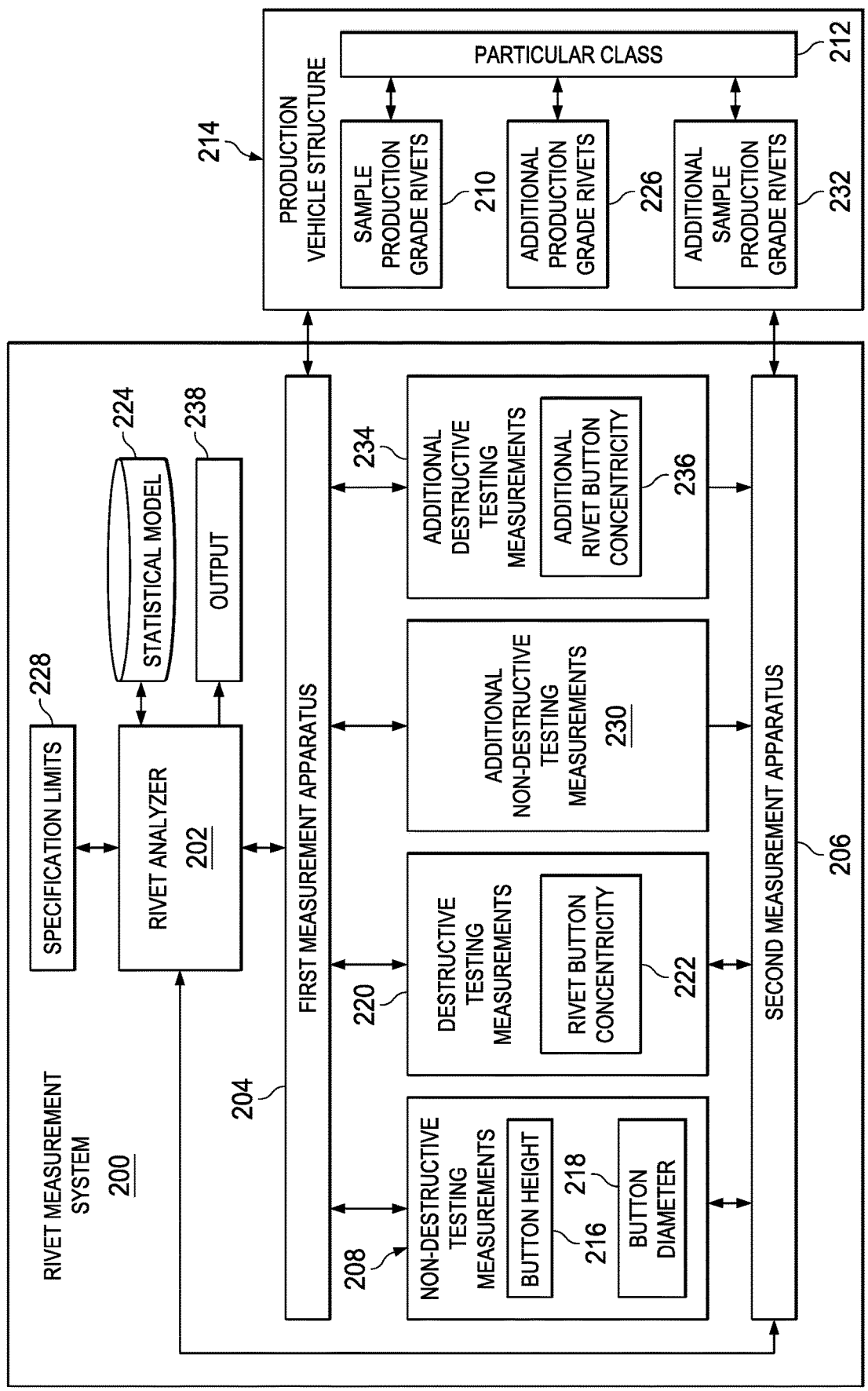
FIG. 2 is an illustration of a block diagram of a rivet measurement system for non-destructive testing of production rivets for a production structure in accordance with an illustrative embodiment.

With reference next to FIG. 2, an illustration of a block diagram of a rivet measurement system for non-destructive testing of production rivets for a production structure is depicted in accordance with an illustrative embodiment. In this illustrative example, rivet measurement system 200 is an example of one implementation for fastener measurement system 102 in FIG. 1.

As depicted, rivet measurement system 200 includes rivet analyzer 202, first measurement apparatus 204, and second measurement apparatus 206. Rivet analyzer 202 is an example of one implementation for analyzer 122 in FIG. 1, that is directed to predict measurements and analysis of production grade rivets. First measurement apparatus 204 and second measurement apparatus 206 are located in testing system 120 in FIG. 1.

As depicted, first measurement apparatus 204 is configured to acquire non-destructive testing measurements 208 for sample production grade rivets 210 of particular class 212 installed in production vehicle structure 214. In this example, non-destructive testing measurements 208 include parameters for rivets, such as button height 216 and button diameter 218. The button for a rivet is the portion of the rivet that forms on an inner surface of the structure. The outer surface of the structure is the side from which the rivet is inserted and the inner surface of the structure is the opposite side of the structure from the outer surface.

As depicted, button height 216 is the height of the rivet button extending beyond the base material surface. Button diameter 218 is the width of the button. For example, button diameter 218 may be measured as the average width of the button at 0 degrees and 90 degrees.

In the illustrative example, second measurement apparatus 206 is configured to acquire destructive testing measurements 220 for sample production grade rivets 210 of particular class 212. With these types of fasteners, sample production grade rivets 210 are drilled out and removed. As depicted, destructive testing measurements 220 include rivet button concentricity 222. Rivet button concentricity 222 describes how symmetrical the button is in the rivet.

As depicted, rivet analyzer 202 is configured to create statistical model 224 representing a relationship between non-destructive testing measurements 208 and destructive testing measurements 220 of sample production grade rivets 210. In creating statistical model 224, rivet analyzer 202 fits a linear expression representing the relationship between destructive testing measurements 220 and non-destructive testing measurements 208 for sample production grade rivets 210 resulting in statistical model 224 achieving an R-squared value of at least a predetermined acceptance threshold. As depicted, statistical model 224 employs a least-squares linear regression and is used to define a linear expression representing the relationship between non-destructive testing measurements 208 and destructive testing measurements 220 of sample production grade rivets 210. Once created, statistical model 224 may be used to predict destructive testing measurements 220 from non-destructive testing measurements 208.

In this illustrative example, rivet analyzer 202 is further configured to acquire non-destructive testing measurements 208 for button height 216 and button diameter 218 for additional production grade rivets 226 of particular class 212 installed in production vehicle structure 214. Rivet analyzer 202 is also further configured to predict rivet button concentricity 222 for additional production grade rivets 226 from non-destructive testing measurements 208 for button height 216 and button diameter 218 using statistical model 224.

Rivet analyzer 202 also may be further configured to determine whether additional production grade rivets 226 installed in production vehicle structure 214 are acceptable by comparing rivet button concentricity 222 predicted for additional production grade rivets 226 to specification limits 228 for particular class 212. In this manner, rivet analyzer 202 enables non-destructive testing measurements 208 of additional production grade rivets 226 to specification limits 228 without having to perform destructive testing.

Additionally, validation of statistical model 224 also may be performed. As depicted, rivet analyzer 202 is configured to validate statistical model 224 by acquiring additional non-destructive testing measurements 230 for additional sample production grade rivets 232 of particular class 212 installed in production vehicle structure 214. Additional non-destructive testing measurements 230 include a measure of button height 216 and button diameter 218. Rivet analyzer 202 is also configured to acquire additional destructive testing measurements 234 for additional sample production grade rivets 232. In this illustrative example, additional sample production grade rivets 232 are drilled out and removed and additional destructive testing measurements 234 include additional rivet button concentricity 236.

Further, rivet analyzer 202 is configured to predict additional rivet button concentricity 236 for additional sample production grade rivets 232 from button height 216 and button diameter 218 measured in statistical model 224. Rivet analyzer 202 is configured to compare additional rivet button concentricity 236 predicted by additional destructive testing measurements 234 for additional sample production grade rivets 232 that include additional rivet button concentricity 236 to assess a predictive capability of statistical model 224.

In this manner, a determination is made as to how well or how accurate statistical model 224 is in predicting destructive testing measurements 220, such as rivet button concentricity 222. Thus, rivet analyzer 202 or some other component may refine statistical model 224 through the inclusion of additional destructive testing measurements 234 and additional non-destructive testing measurements 230 for additional sample production grade rivets 232 of particular class 212 installed in production vehicle structure 214.

Further, rivet analyzer 202 generates output 238 indicating whether the non-destructive testing measurements of the production grade rivets installed on the vehicle structure satisfy specification limits 228.

The illustration of measurement environment 100 in FIG. 1 and the measurement systems that may be used in measurement environment 100 in FIG. 1 and rivet measurement system 200 in FIG. 2 are not meant to imply physical or architectural limitations to the manner in which an illustrative embodiment may be implemented. Other components, in addition to or in place of the ones illustrated, may be used. Some components may be unnecessary. Also, the blocks are presented to illustrate some functional components. One or more of these blocks may be combined, divided, or combined and divided into different blocks when implemented in an illustrative embodiment.

For example, other types of non-destructive testing measurements may be made or predicted, in addition to or in place of rivet button concentricity, such as a rivet flushness. In the illustrative examples, flushness for a rivet is the height of the rivet head above the surface of the structure in which the rivet is installed.

For example, another type of destructive testing measurement that may be predicted is interference for rivets. In this illustrative example, interference is the difference in the diameter of the hole between pre-installation and post installation of the rivet. In other words, interference is the measure of hole expansion due to rivet installation at specific locations.

Further, the different features described with respect to rivet measurement system 200 in FIG. 2 may be applied to other types of fasteners, other than rivets. For example, different features described in rivet measurement system 200 in FIG. 2 may be applied to fasteners such as bolts, screws, threaded fasteners, or other suitable types of fasteners.

Further, different type of fasteners will have different characteristics that may be measured. For instance, unlike rivets, bolts do not have buttons to measure. When fasteners 106 in FIG. 1 take the form of bolts, measurements may include head height, pin protrusion, and other characteristics of bolts.

Figure 3:
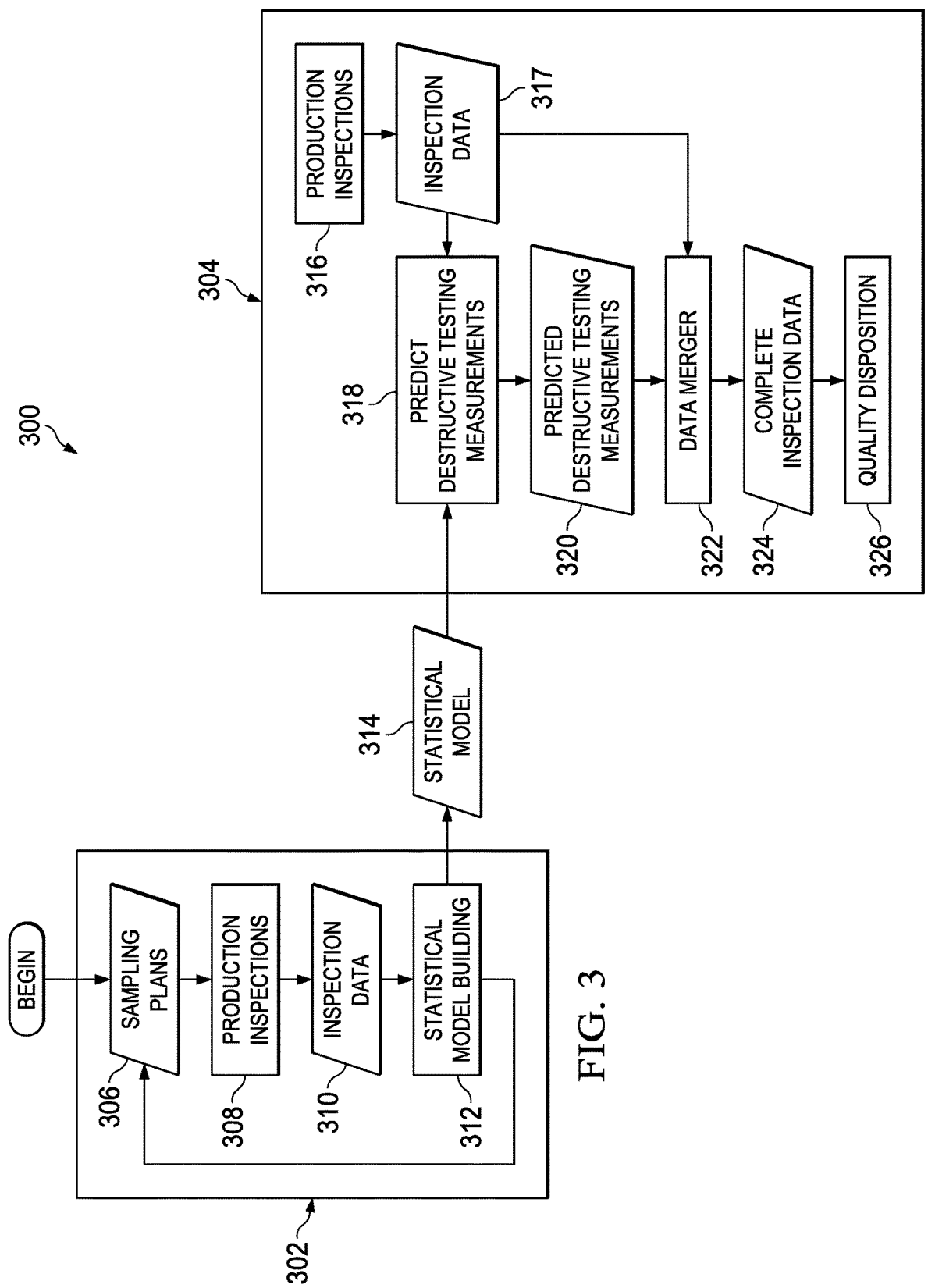
FIG. 3 is an illustration of a data flow diagram for a rivet measurement system in accordance with an illustrative embodiment.

With reference next to FIG. 3, an illustration of a data flow diagram for a rivet measurement system is depicted in accordance with an illustrative embodiment. Data flow 300, in this figure, may be implemented in a fastener measurement system, such as fastener measurement system 102 in FIG. 1 or rivet measurement system 200 in FIG. 2.

In this illustrative example, data flow 300 includes training phase 302 and production phase 304. The data flow begins in training phase 302 by identifying sampling plans 306. Sampling plans 306 indicate measurements that are to be made for fasteners installed in a structure.

Production inspections are performed in block 308 resulting in inspection data 310. Inspection data 310 includes destructive testing measurements, non-destructive testing measurements, and optionally environmental factors. Next, statistical model building 312 occurs in which a statistical model is built in block 312 resulting in current statistical model 314.

In production phase 304, production inspections are performed in block 316 which includes non-destructive testing of production structures. Inspection data 317 is generated as a result of the production inspections performed in block 316. Inspection data 317 includes non-destructive testing measurements and also may optionally include environmental factors. These environmental factors may include particular equipment, the status of the equipment, maintenance records for the equipment, and other suitable types of information.

In this illustrative example, statistical model 314, generated in training phase 302, predicts destructive testing measurements in block 318, resulting in predicted destructive testing measurements 320.

Predictive destructive testing measurements 320 and inspection data 317 are merged for analysis in block 322 to produce complete inspection data 324. As depicted, complete inspection data 324 includes predicted destructive testing measurements, non-destructive testing measurements, and optionally environmental factors that may be obtained from inspections.

With complete inspection data 324, quality disposition is performed in block 326. The quality disposition may indicate whether the production structure in question meets specification limits for the production structure with respect to the installation of fasteners.

Figure 4:
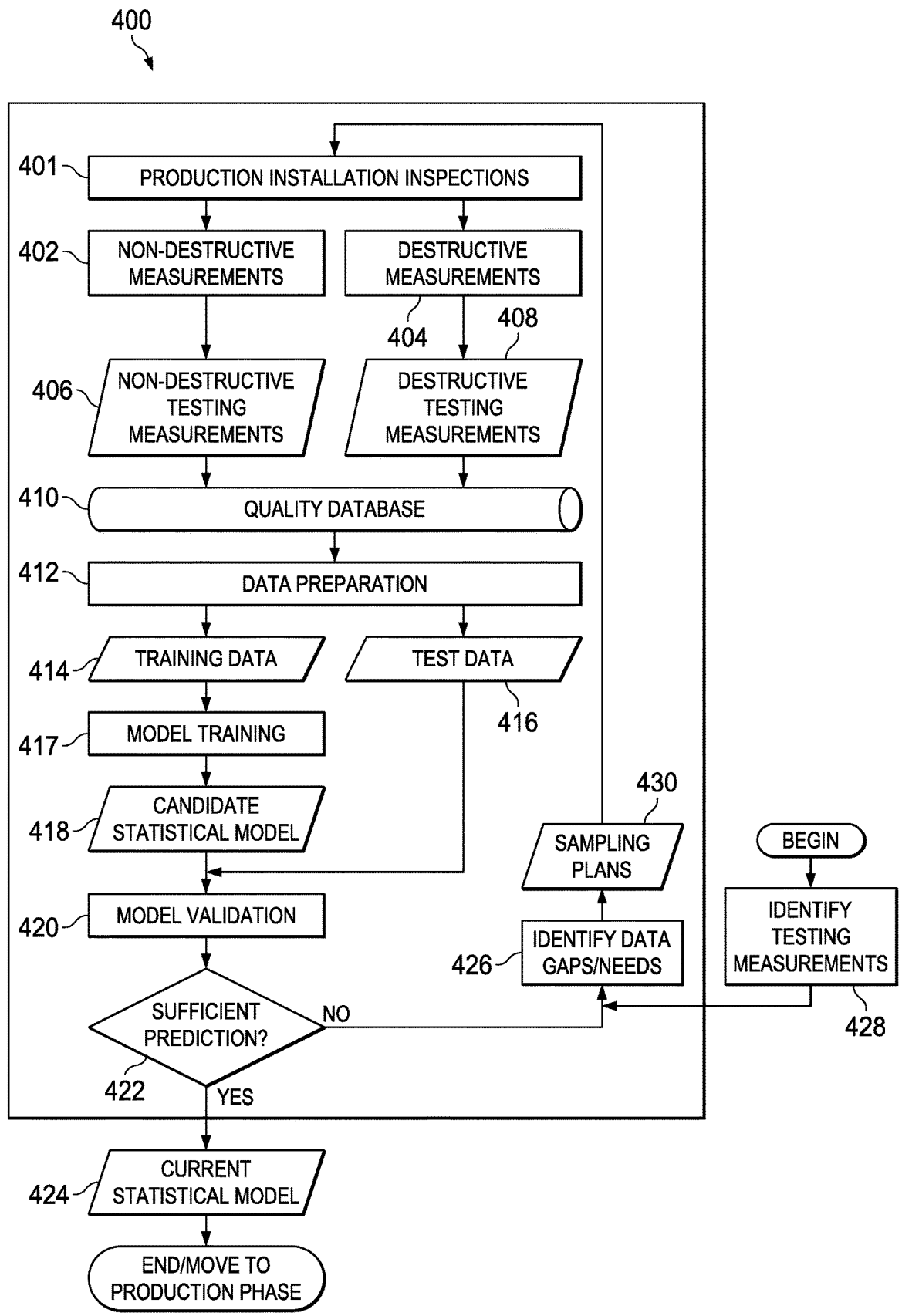
FIG. 4 is an illustration of a data flow diagram for building a statistical model in accordance with an illustrative embodiment.

With reference next to FIG. 4, an illustration of a data flow diagram for building a statistical model is depicted in accordance with an illustrative embodiment. Data flow 400 is an iterative data flow for building a statistical model, such as statistical model 132 in FIG. 1 or statistical model 224 in FIG. 2.

The process begins by identifying testing measurements of interest in block 428. The process then identifies data gaps or needs of the characteristics in block 426. The results of this identification in block 426 are sampling plans 430. Sampling plans 430 include identification and types of measurements to be made.

Production installation inspections are performed in block 401 using sampling plans 430. These inspections may be on production structures for a vehicle. In this illustrative example, non-destructive testing measurements are performed in block 402 and destructive testing measurements are performed in block 404. The result of these measurements is non-destructive testing measurements 406 and destructive testing measurements 408, respectively. Additionally, environmental factors also may be obtained from the inspections.

The measurements are stored in quality database 410. Data preparation is then performed in block 412. Data preparation 412 may include placing data in the appropriate groupings and formats for generating a statistical model. In this illustrative example, the result of data preparation in block 412 is training data 414 and test data 416. Training data 414 is used in model training 417 to generate candidate statistical model 418.

Model validation is performed in block 420 using candid statistical model 418 and test data 416. In model validation 420, the validation uses test data 416 to determine how well candidate statistical model 418 predicts destructive testing measurements 408. Test data 416 includes actual measured destructive testing measurements 408 for which predicted destructive testing measurements are made through candidate statistical model 418. The correlation between test data 416 and the predicted destructive test measurements may be identified through Model validation 420.

A determination is made as to whether candidate statistical model 418 sufficiently predicts destructive testing measurements 408 in block 422. If a sufficient prediction is present, candidate statistical model 418 is designated as current statistical model 424 with the data flow ending.

If candidate statistical model 418 is not sufficient, the process returns to block 426 until the process identifies data gaps and other needs in block 426. If the predictive ability of the model is not sufficient, then new data may be collected. Specifically, if areas of the input parameter space which have not been sufficiently measured are present, then this situation is a data gap and additional sampling for these specific input parameters will be required for model calibration. This also includes additional variables that were not previously recorded. For example, if the model is not sufficient with the variables present, then data is collected with additional variables. Thus, if flushness was not recorded and the model did not perform as desired, then additional sampling with flushness information included may be required.

Figure 5:
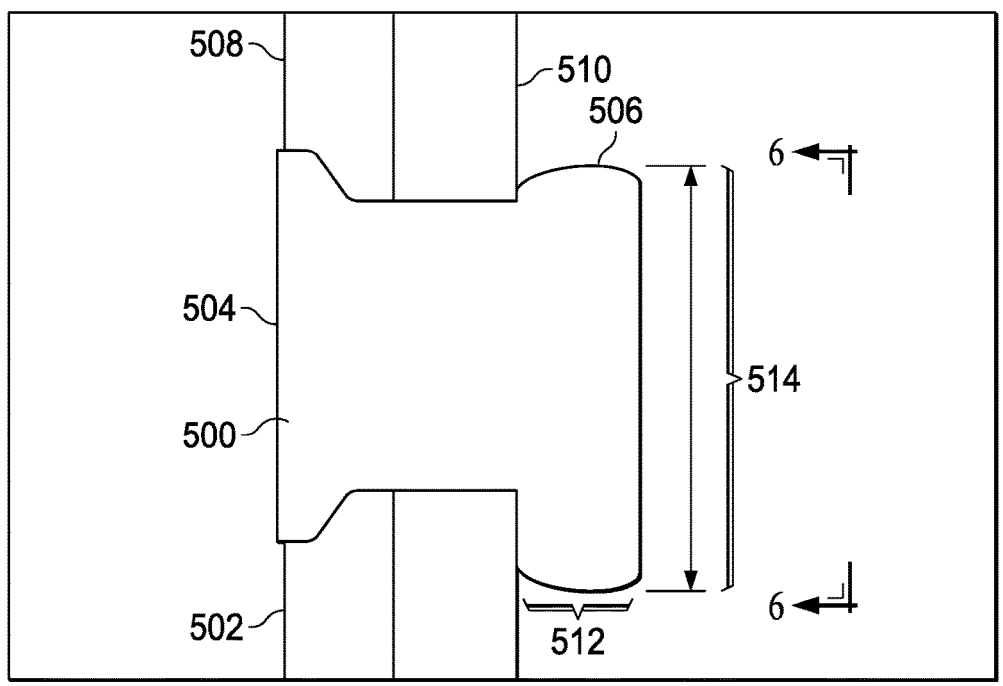
FIG. 5 is an illustration of an installed rivet in accordance with an illustrative embodiment.

With reference to FIG. 5, an illustration of an installed rivet is depicted in accordance with an illustrative embodiment. In this illustrative example, a cross-sectional view of rivet 500 is installed in structure 502. Rivet 500 has head 504 and button 506. As seen, head 504 is on outer surface 508, which is the surface through which rivet 500 is inserted for installation. Inner surface 510 is opposite to outer surface 508 and is the surface on which button 506 forms when rivet 500 is installed. In this illustrative example, button 506 has button height 512 and button diameter 514.

Figure 6:
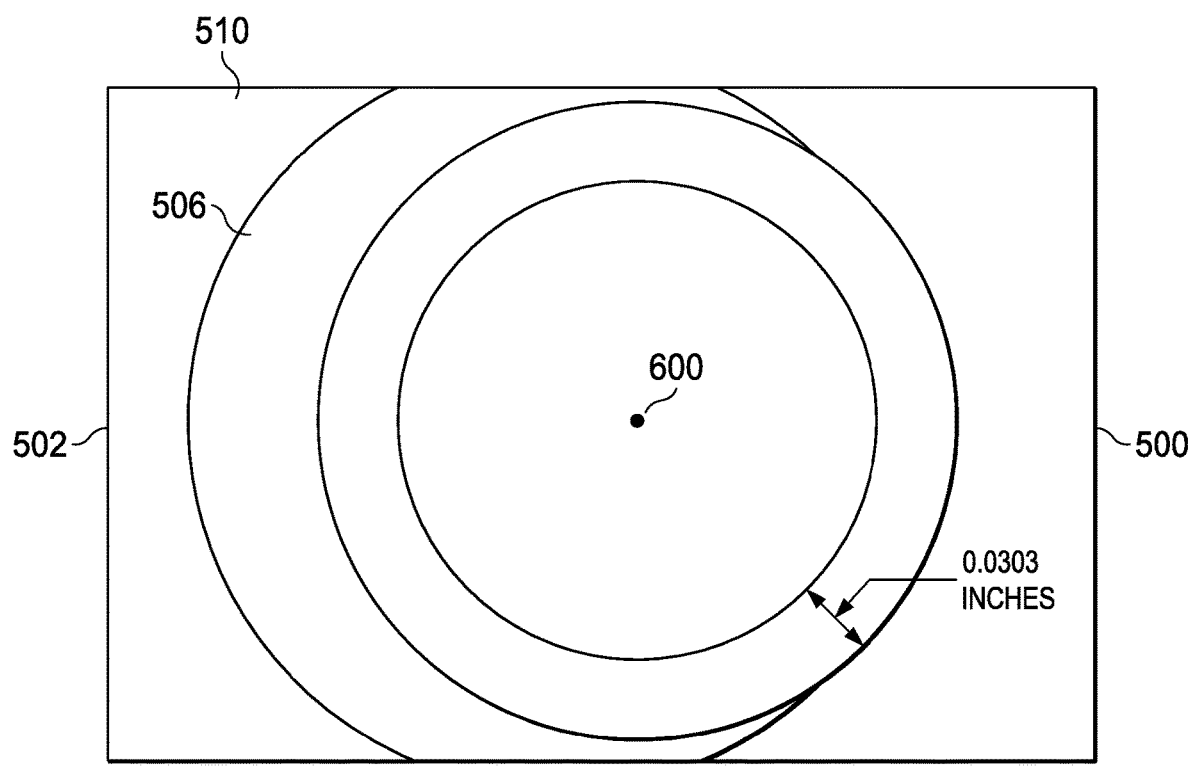
FIG. 6 is an illustration of an end view of a button in an installed rivet in accordance with an illustrative embodiment.

With reference now to FIG. 6, an illustration of an end view of a button in an installed rivet is depicted in accordance with an illustrative embodiment. In this illustrative example, a view of button 506 is shown in the direction of lines 6-6 in FIG. 5. In this illustrative example, concentricity is the symmetry of button 506 about axis 600.

Figure 7:
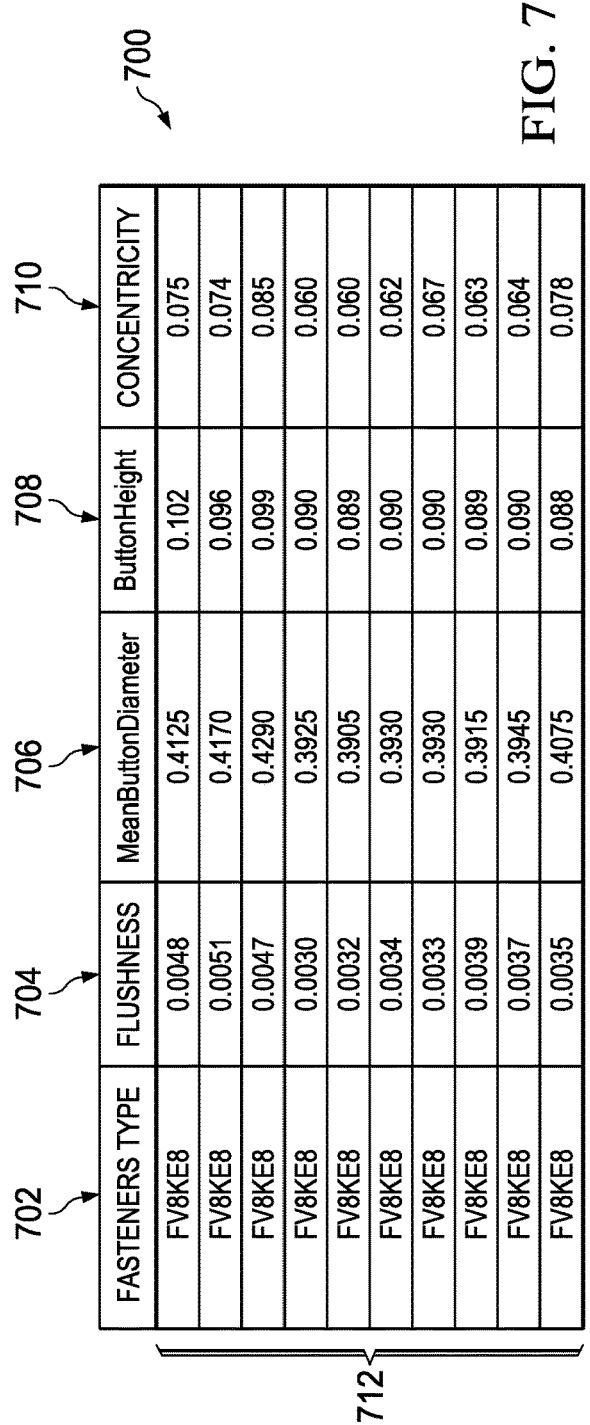
FIG. 7 is an illustration of a table of rivet data in accordance with an illustrative embodiment.

With reference now to FIG. 7, an illustration of a table of rivet data is depicted in accordance with an illustrative embodiment. In this illustrative example, table 700 includes data from non-destructive testing measurements and destructive testing measurements made for rivets installed in a structure, such as a production aircraft fuselage. These rivets are examples of sample production grade rivets 210 and additional sample production grade rivets 232 in FIG. 2.

As depicted, table 700 includes columns for fasteners type 702, flushness 704, mean button diameter 706, button height 708, and concentricity 710. Rows 712 are entries for measurements made of installed rivets.

As depicted, flushness 704, mean button diameter 706, and button height 708 are non-destructive testing measurements. Concentricity 710 is destructive testing measurements for the rivets.

Figure 8:
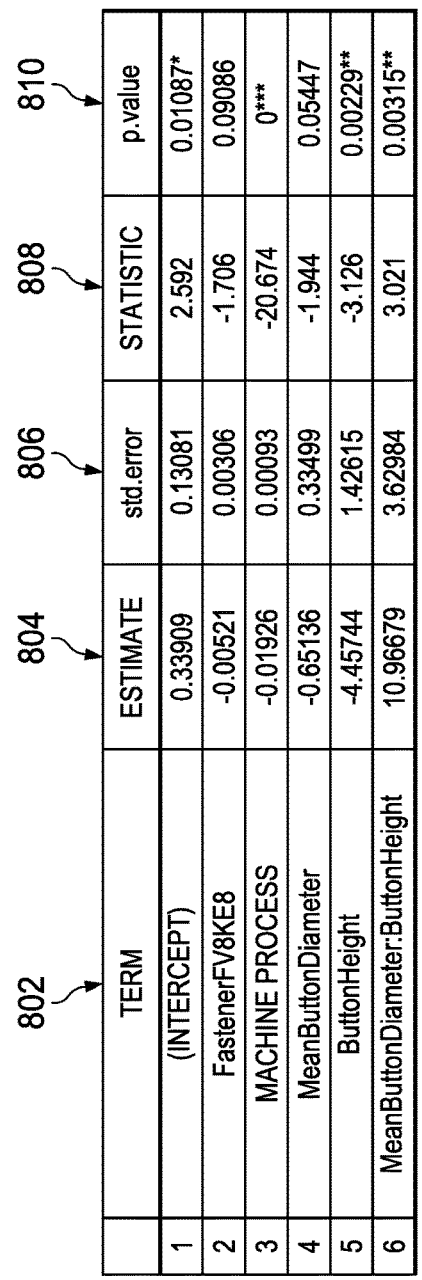
FIG. 8 is an illustration of a table for a statistical model for concentricity in accordance with an illustrative embodiment.

With reference now to FIG. 8, an illustration of a table for a statistical model for concentricity is depicted in accordance with an illustrative embodiment. In this illustrative example, table 800 contains data for a statistical model. This statistical model is a linear model for concentricity. More specifically, the statistical model in table 800 is a least-squares regression to fit a linear model for concentricity developed using non-destructive testing measurements and destructive testing measurements in table 700 in FIG. 7.

As depicted, table 800 includes the following columns: TERM 802, ESTIMATE 804, std.error 806, STATISTIC 808, and p.value 810 that describe the statistical model using the following equation for concentricity:

$$\text{Concentricity} = \beta_0 + \beta_1 \times \text{Fastener} + \beta_2 * \text{MachineProcess} + \beta_3 * \text{ButtonDiameter} + \beta_4 * \text{ButtonHeight} + \beta_5 * \text{ButtonDiameter} \times \text{ButtonHeight}$$

The statistical model may be generated using observed non-destructive rivet measurements to estimate the coefficients ($\beta_1$-$\beta_5$) via a mathematical technique such as least squares regression. As these coefficients are estimated from data with inherent variability, the degree of confidence in these estimates are represented as well as their statistical significance. Table 800 for the statistical model includes this information. For each row in table 800, TERM 802 indicates which term in the equation for concentricity is represented by that row. ESTIMATE 804 gives the statistical estimate for the $\beta$ coefficient for the term. Next, std.error 808 represents the standard error, a measure of confidence, associated with the $\beta$ estimate. STATISTIC 808 and p.value 810 capture the statistical significance of the $\beta$ estimate.

Figure 9:
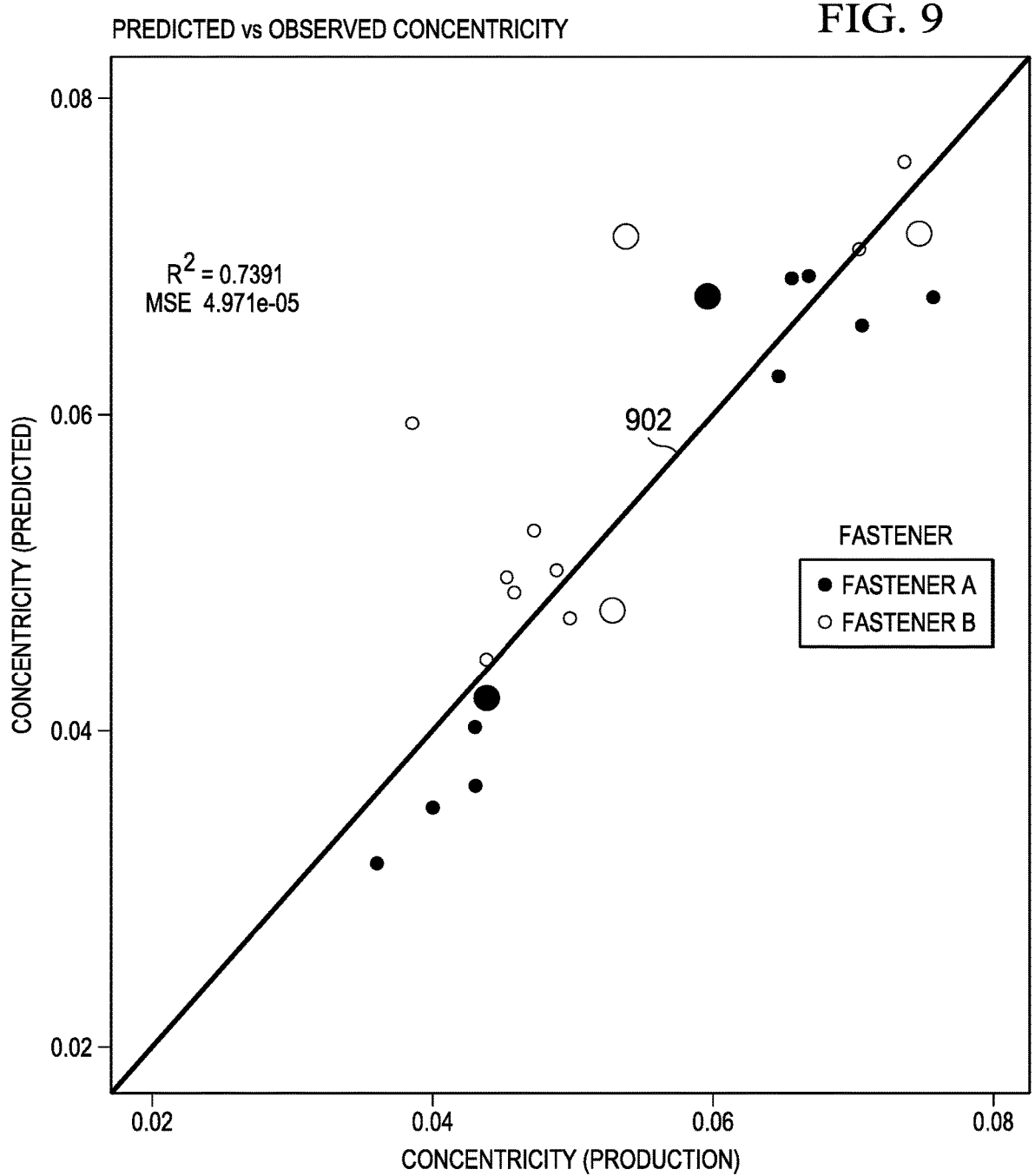
FIG. 9 is an illustration of a graph showing predicted versus measured concentricity in accordance with an illustrative embodiment.

With reference next to FIG. 9, an illustration of a graph showing predicted versus measured concentricity is depicted in accordance with an illustrative embodiment. In this illustrative example, graph 900 is a visualization of statistical model 800 shown in FIG. 8. In this example, line 902 in graph 900 is generated based on statistical model 800 in FIG. 8. The data points in graph 900 shows measured concentricity taken from destructive testing measurements of rivets relative to the predicted concentricity based on statistical model 800 in FIG. 8. Line 902 indicates where points should fall if the model produced predictions without errors for the same rivets installed in a structure.

Figure 10:
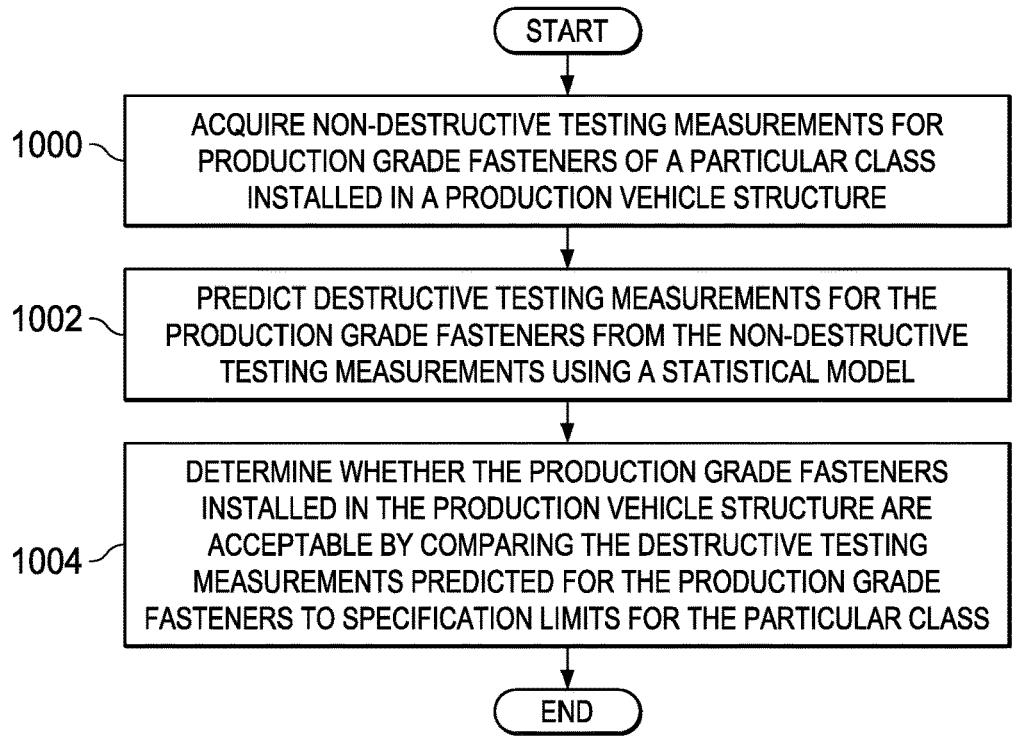
FIG. 10 is an illustration of a flowchart of a process for non-destructive testing of production grade fasteners in accordance with an illustrative embodiment.

Turning next to FIG. 10, an illustration of a flowchart of a process for non-destructive testing of production grade fasteners is depicted in accordance with an illustrative embodiment. The process illustrated in FIG. 10 may be implemented using analyzer 122 in FIG. 1. The different operations in this flowchart may be implemented using at least one of program code or hardware to perform the operations. Program code may then be run on a processor unit in a computer system.

The process begins by acquiring non-destructive testing measurements for production grade fasteners of a particular class installed in a production vehicle structure (operation 1000). The process predicts destructive testing measurements for the production grade fasteners from the non-destructive testing measurements using a statistical model (operation 1002). The statistical model represents a relationship between the non-destructive testing measurements and the destructive testing measurements of the production grade fasteners.

The process determines whether the production grade fasteners installed in the production vehicle structure are acceptable by comparing the destructive testing measurements predicted for the production grade fasteners to specification limits for the particular class (operation 1004). The process terminates thereafter. In this manner, the different operations in this flowchart enable non-destructive testing measurements of additional production grade fasteners to the specification limits without having to perform destructive testing.

Figure 11:
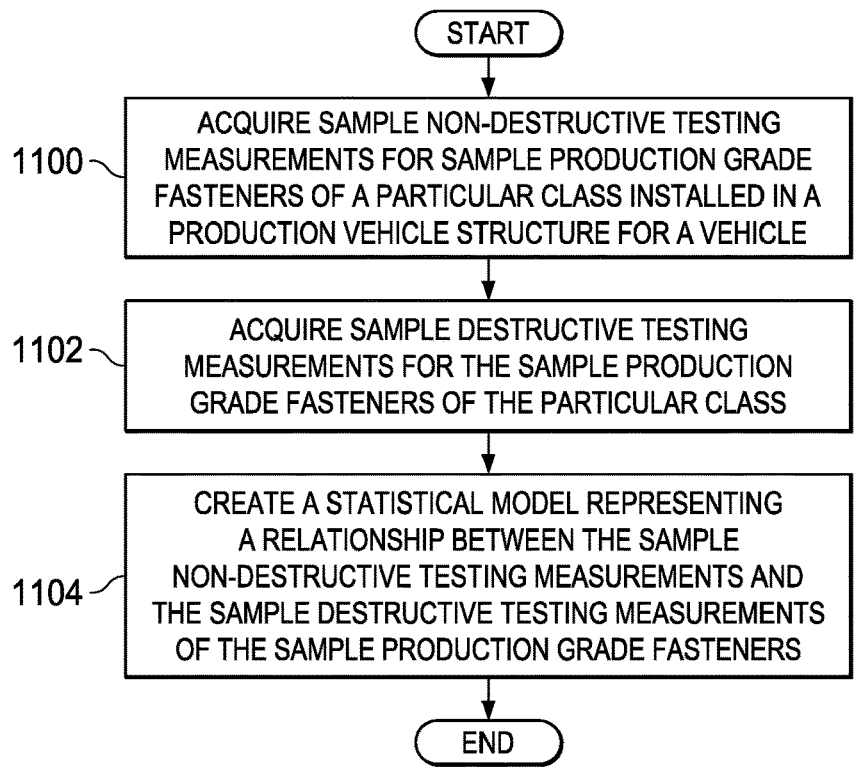
FIG. 11 is an illustration of a flowchart of a process for creating a statistical model in accordance with an illustrative embodiment.

With reference now to FIG. 11, an illustration of a flowchart of a process for creating a statistical model is depicted in accordance with an illustrative embodiment. The process illustrated in FIG. 11 may be implemented using analyzer 122 in FIG. 1. The different operations in this flowchart may be implemented using at least one of program code or hardware to perform the operations.

The process begins by acquiring sample non-destructive testing measurements for sample production grade fasteners of a particular class installed in a production vehicle structure for a vehicle (operation 1100). The process acquires sample destructive testing measurements for the sample production grade fasteners of the particular class (operation 1102). The sample production grade fasteners are removed for the destructive testing measurements.

The process creates a statistical model representing a relationship between the sample non-destructive testing measurements and the sample destructive testing measurements of the sample production grade fasteners (operation 1104). The process terminates thereafter. The statistical model may be used to predict destructive testing measurements from non-destructive testing measurements made for the fasteners. In this manner, the statistical model enables making non-destructive testing measurements through a prediction of the destructive testing measurements using the non-destructive testing measurements and the statistical model.

Figure 12:
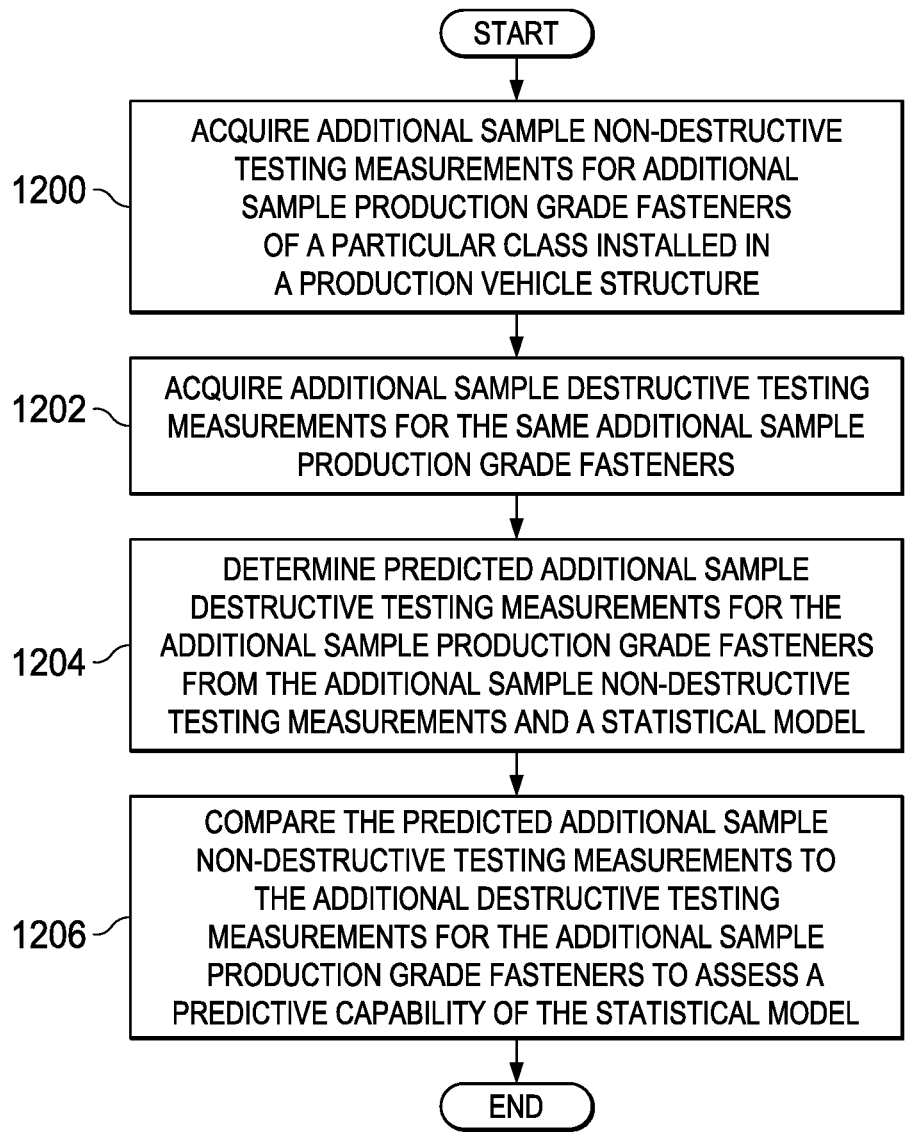
FIG. 12 is an illustration of a flowchart of a process for validating a statistical model in accordance with an illustrative embodiment.

With reference now to FIG. 12, an illustration of a flowchart of a process for validating a statistical model is depicted in accordance with an illustrative embodiment. The process illustrated in FIG. 12 may be implemented using analyzer 122 in FIG. 1. The different operations in this flowchart may be implemented using at least one of program code or hardware to perform the operations. Program code may then be run on a processor unit in a computer system.

The process begins by acquiring additional sample non-destructive testing measurements for additional sample production grade fasteners of a particular class installed in a production vehicle structure (operation 1200). The process acquires additional sample destructive testing measurements for the same additional sample production grade fasteners (operation 1202). The additional sample production grade fasteners are drilled out and removed for making the measurements.

The process determines predicted additional sample destructive testing measurements for the additional sample production grade fasteners from the additional sample non-destructive testing measurements and a statistical model (operation 1204). The process compares the predicted additional sample non-destructive testing measurements to the additional destructive testing measurements for the additional sample production grade fasteners to assess a predictive capability of the statistical model (operation 1206). The process terminates thereafter. In this manner, the process in this flowchart may be used to determine how accurate or how well the statistical model is able to predict destructive testing measurements.

Figure 13:
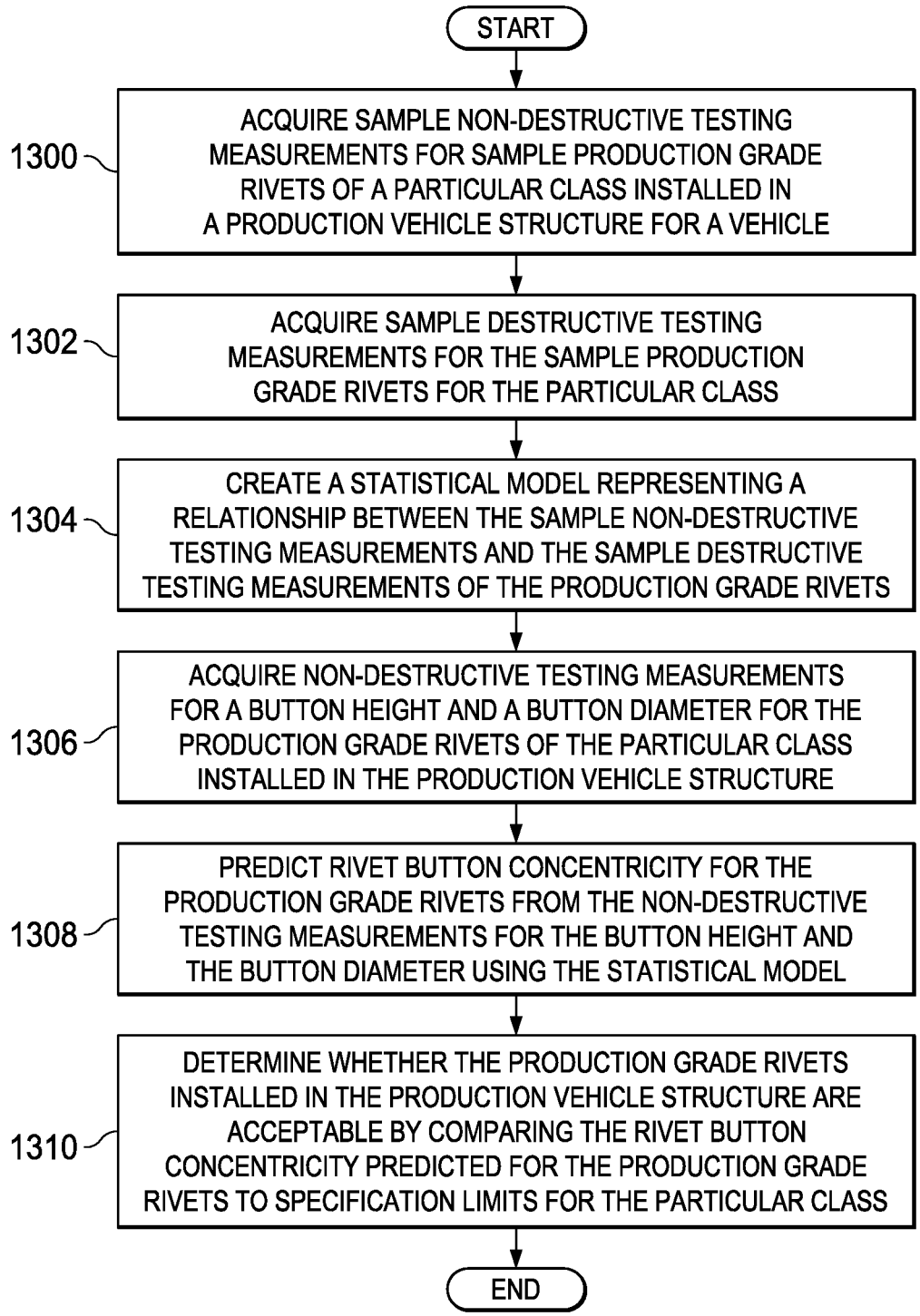
FIG. 13 is an illustration of a flowchart of a process for non-destructive testing measurements of production rivets for a production vehicle structure in accordance with an illustrative embodiment.

Turning now to FIG. 13, an illustration of a flowchart of a process for non-destructive testing measurements of production rivets for a production vehicle structure is depicted in accordance with an illustrative embodiment. The process illustrated in FIG. 13 may be implemented using analyzer 122 in FIG. 1. The different operations in this flowchart may be implemented using at least one of program code or hardware to perform the operations. Program code may then be run on a processor unit in a computer system.

The process begins by acquiring sample non-destructive testing measurements for sample production grade rivets of a particular class installed in a production vehicle structure for a vehicle (operation 1300). The non-destructive testing measurements include a button height and a button diameter. The process acquires sample destructive testing measurements for the sample production grade rivets of the particular class (operation 1302). The sample production grade rivets are drilled out and removed, and the sample destructive testing measurements include a rivet button concentricity.

The process creates a statistical model representing a relationship between the sample non-destructive testing measurements and the sample destructive testing measurements of the production grade rivets (operation 1304). The process acquires non-destructive testing measurements for a button height and a button diameter for the production grade rivets of the particular class installed in the production vehicle structure (operation 1306). The process predicts rivet button concentricity for the production grade rivets from the non-destructive testing measurements for the button height and the button diameter using the statistical model (operation 1308).

The process determines whether the production grade rivets installed in the production vehicle structure are acceptable by comparing the rivet button concentricity predicted for the production grade rivets to specification limits for the particular class (operation 1310). The process terminates thereafter. The operations in this flowchart enable non-destructive testing measurements of production grade rivets to determine whether the production grade rivets meet the specification limits without having to perform destructive testing.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent at least one of a module, a segment, a function, or a portion of an operation or step. For example, one or more of the blocks may be implemented as program code, hardware, or a combination of the program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware. Each block in the flowcharts or the block diagrams may be implemented using special purpose hardware systems that perform the different operations or combinations of special purpose hardware and program code run by the special purpose hardware.

In some alternative implementations of an illustrative embodiment, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added, in addition to the illustrated blocks, in a flowchart or block diagram.

Figure 14:
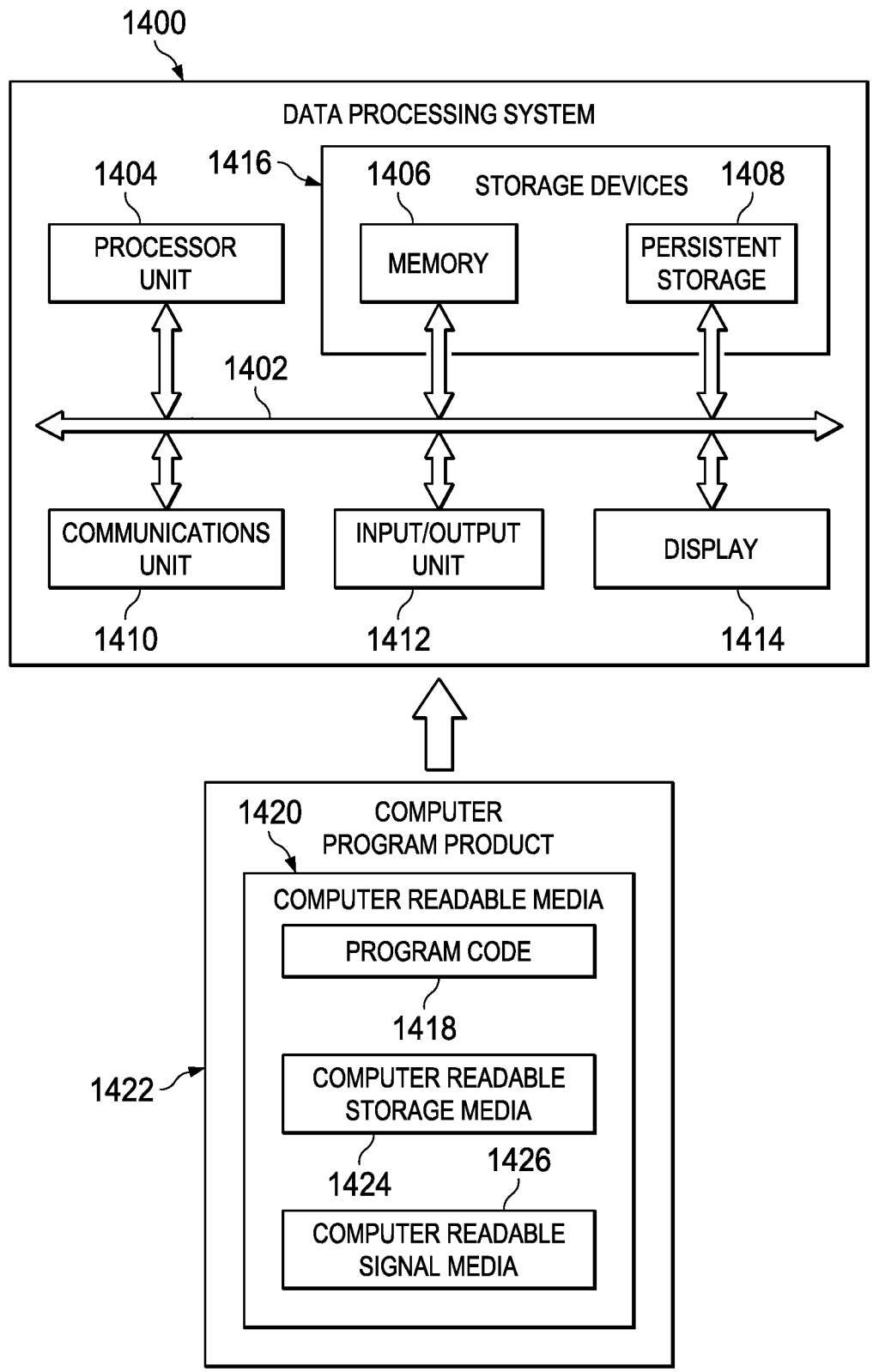
FIG. 14 is an illustration of a block diagram of a data processing system in accordance with an illustrative embodiment.

Turning now to FIG. 14, an illustration of a block diagram of a data processing system is depicted in accordance with an illustrative embodiment. Data processing system 1400 may be used to implement computer system 136 in FIG. 1. In this illustrative example, data processing system 1400 includes communications framework 1402, which provides communications between processor unit 1404, memory 1406, persistent storage 1408, communications unit 1410, input/output unit 1412, and display 1414. In this example, communications framework 1402 may take the form of a bus system.

Processor unit 1404 serves to execute instructions for software that may be loaded into memory 1406. Processor unit 1404 may be a number of processors, a multi-processor core, or some other type of processor, depending on the particular implementation.

Memory 1406 and persistent storage 1408 are examples of storage devices 1416. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 1416 may also be referred to as computer readable storage devices in these illustrative examples. Memory 1406, in these examples, may be, for example, a random-access memory or any other suitable volatile or non-volatile storage device. Persistent storage 1408 may take various forms, depending on the particular implementation.

For example, persistent storage 1408 may contain one or more components or devices. For example, persistent storage 1408 may be a hard drive, a solid state hard drive, a flash memory, a rewritable optical disk, a rewritable magnetic tape, or some combination of the above. The media used by persistent storage 1408 also may be removable. For example, a removable hard drive may be used for persistent storage 1408.

Communications unit 1410, in these illustrative examples, provides for communications with other data processing systems or devices. In these illustrative examples, communications unit 1410 is a network interface card.

Input/output unit 1412 allows for input and output of data with other devices that may be connected to data processing system 1400. For example, input/output unit 1412 may provide a connection for user input through at least one of a keyboard, a mouse, or some other suitable input device. Further, input/output unit 1412 may send output to a printer. Display 1414 provides a mechanism to display information to a user.

Instructions for at least one of the operating system, applications, or programs may be located in storage devices 1416, which are in communication with processor unit 1404 through communications framework 1402. The processes of the different embodiments may be performed by processor unit 1404 using computer implemented instructions, which may be located in a memory, such as memory 1406.

These instructions are referred to as program code, computer usable program code, or computer readable program code that may be read and executed by a processor in processor unit 1404. The program code in the different embodiments may be embodied on different physical or computer readable storage media, such as memory 1406 or persistent storage 1408.

Program code 1418 is located in a functional form on computer readable media 1420 that is selectively removable and may be loaded onto or transferred to data processing system 1400 for execution by processor unit 1404. Program code 1418 and computer readable media 1420 form computer program product 1422 in these illustrative examples. In one example, computer readable media 1420 may be computer readable storage media 1424 or computer readable signal media 1426.

In these illustrative examples, computer readable storage media 1424 is a physical or tangible storage device used to store program code 1418 rather than a medium that propagates or transmits program code 1418.

Alternatively, program code 1418 may be transferred to data processing system 1400 using computer readable signal media 1426. Computer readable signal media 1426 may be, for example, a propagated data signal containing program code 1418. For example, computer readable signal media 1426 may be at least one of an electromagnetic signal, an optical signal, or any other suitable type of signal. These signals may be transmitted over at least one of communications links, such as wireless communications links, optical fiber cable, coaxial cable, a wire, or any other suitable type of communications link.

The different components illustrated for data processing system 1400 are not meant to provide architectural limitations to the manner in which different embodiments may be implemented. The different illustrative embodiments may be implemented in a data processing system including components, in addition to or in place of those illustrated, for data processing system 1400. Other components shown in FIG. 14 can be varied from the illustrative examples shown. The different embodiments may be implemented using any hardware device or system capable of running program code 1418.

Figure 15:
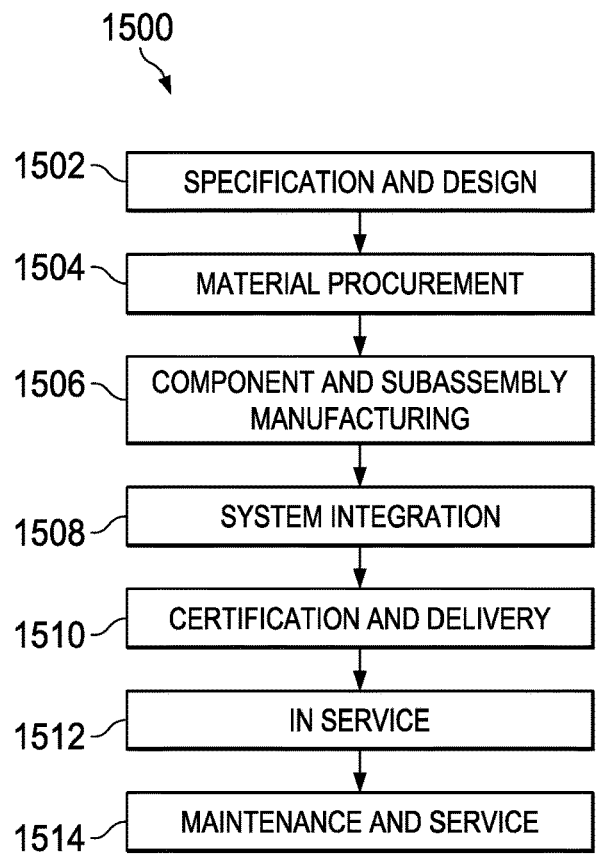
FIG. 15 is an illustration of a block diagram of an aircraft manufacturing and service method in accordance with an illustrative embodiment.
Figure 16:
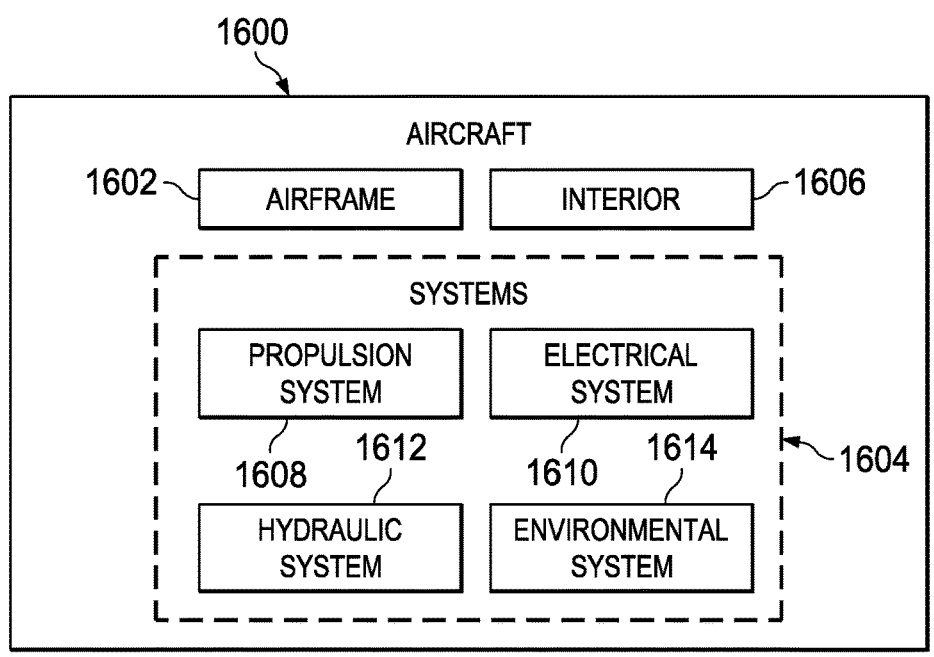
FIG. 16 is an illustration of a block diagram of an aircraft in which an illustrative embodiment may be implemented.

The illustrative embodiments of the present disclosure may be described in the context of aircraft manufacturing and service method 1500 as shown in FIG. 15 and aircraft 1600 as shown in FIG. 16. Turning first to FIG. 15, an illustration of a block diagram of an aircraft manufacturing and service method is depicted in accordance with an illustrative embodiment. During pre-production, aircraft manufacturing and service method 1500 may include specification and design 1502 of aircraft 1600 in FIG. 16 and material procurement 1504.

During production, component and subassembly manufacturing 1506 and system integration 1508 of aircraft 1600 in FIG. 16 takes place. Thereafter, aircraft 1600 in FIG. 16 may go through certification and delivery 1510 in order to be placed in service 1512. While in service 1512 by a customer, aircraft 1600 in FIG. 16 is scheduled for routine maintenance and service 1514, which may include modification, reconfiguration, refurbishment, or other maintenance and service.

Each of the processes of aircraft manufacturing and service method 1500 may be performed or carried out by a system integrator, a third party, an operator, or some combination thereof. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 16, an illustration of a block diagram of an aircraft is depicted in which an illustrative embodiment may be implemented. In this example, aircraft 1600 is produced by aircraft manufacturing and service method 1500 in FIG. 15 and may include airframe 1602 with plurality of systems 1604 and interior 1606. Examples of systems 1604 include one or more of propulsion system 1608, electrical system 1610, hydraulic system 1612, and environmental system 1614. Any number of other systems may be included. Although an aerospace example is shown, different illustrative embodiments may be applied to other industries, such as the automotive industry.

The apparatuses and methods embodied herein may be employed during at least one of the stages of aircraft manufacturing and service method 1500 in FIG. 15.

In one illustrative example, components or subassemblies produced in component and subassembly manufacturing 1506 in FIG. 15 may be fabricated or manufactured in a manner similar to components or subassemblies produced while aircraft 1600 is in service 1512 in FIG. 15. As yet another example, one or more apparatus embodiments, method embodiments, or a combination thereof may be utilized during production stages, such as component and subassembly manufacturing 1506 and system integration 1508 in FIG. 15. One or more apparatus embodiments, method embodiments, or a combination thereof may be utilized while aircraft 1600 is in service 1512, during maintenance and service 1514 in FIG. 15, or both. For example, inspection of fasteners may be performed using a fastener measurement system during component and subassembly manufacturing 1506 to inspect the installation of fasteners. Additionally, the measurement system also may be used during maintenance and service 1514 to inspect already installed fasteners, fasteners installed during routine maintenance including reconfiguration, refurbishment, and other maintenance or service.

The use of a number of the different illustrative embodiments may substantially expedite the assembly of aircraft 1600, reduce the cost of aircraft 1600, or both expedite the assembly of aircraft 1600 and reduce the cost of aircraft 1600. For example, the use of a fastener measurement system, in accordance with an illustrative example, may reduce the time and cost for manufacturing aircraft 1600. For example, the time needed to inspect fasteners may be reduced. In this manner, aircraft 1600 may be manufactured more quickly as compared to using current techniques that involve destructive testing measurements.

Figure 17:
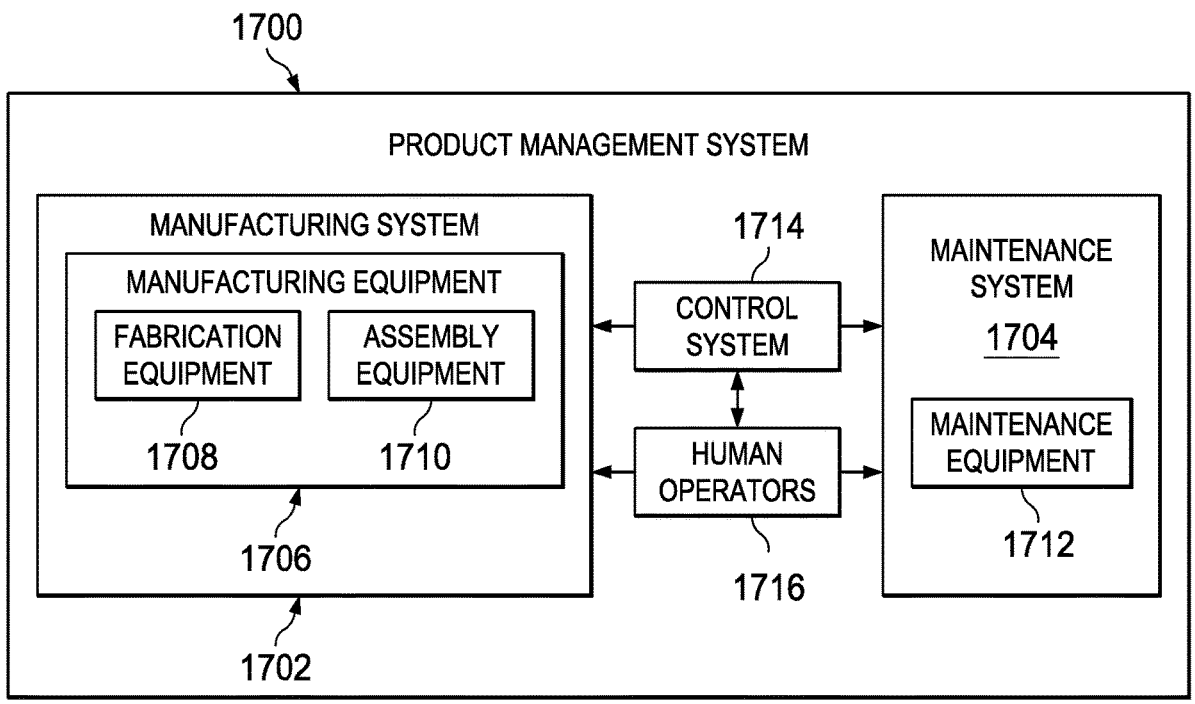
FIG. 17 is an illustration of a block diagram of a product management system in accordance with an illustrative embodiment.

Turning now to FIG. 17, an illustration of a block diagram of a product management system is depicted in accordance with an illustrative embodiment. Product management system 1700 is a physical hardware system. In this illustrative example, product management system 1700 may include at least one of manufacturing system 1702 or maintenance system 1704.

Manufacturing system 1702 is configured to manufacture products, such as aircraft 1600 in FIG. 16. As depicted, manufacturing system 1702 includes manufacturing equipment 1706. Manufacturing equipment 1706 includes at least one of fabrication equipment 1708 or assembly equipment 1710.

Fabrication equipment 1708 is equipment that may be used to fabricate components for parts used to form aircraft 1600 in FIG. 16. For example, fabrication equipment 1708 may include machines and tools. These machines and tools may be at least one of a drill, a hydraulic press, a furnace, a mold, a composite tape laying machine, a vacuum system, a lathe, or other suitable types of equipment. Fabrication equipment 1708 may be used to fabricate at least one of metal parts, composite parts, semiconductors, circuits, fasteners, ribs, skin panels, spars, antennas, or other suitable types of parts.

Assembly equipment 1710 is equipment used to assemble parts to form aircraft 1600 in FIG. 16. In particular, assembly equipment 1710 may be used to assemble components and parts to form aircraft 1600 in FIG. 16. Assembly equipment 1710 also may include machines and tools. These machines and tools may be at least one of a robotic arm, a crawler, a faster installation system, a rail-based drilling system, or a robot. Assembly equipment 1710 may be used to assemble parts such as seats, horizontal stabilizers, wings, engines, engine housings, landing gear systems, and other parts for aircraft 1600 in FIG. 16.

In this illustrative example, maintenance system 1704 includes maintenance equipment 1712. Maintenance equipment 1712 may include any equipment needed to perform maintenance on aircraft 1600 in FIG. 16. Maintenance equipment 1712 may include tools for performing different operations on parts on aircraft 1600 in FIG. 16. These operations may include at least one of disassembling parts, refurbishing parts, inspecting parts, reworking parts, manufacturing replacement parts, or other operations for performing maintenance on aircraft 1600 in FIG. 16. These operations may be for routine maintenance, inspections, upgrades, refurbishment, or other types of maintenance operations.

In the illustrative example, maintenance equipment 1712 may include ultrasonic inspection devices, x-ray imaging systems, vision systems, drills, crawlers, and other suitable device. In some cases, maintenance equipment 1712 may include fabrication equipment 1708, assembly equipment 1710, or both, to produce and assemble parts that may be needed for maintenance.

Product management system 1700 also includes control system 1714. Control system 1714 is a hardware system and may also include software or other types of components. Control system 1714 is configured to control the operation of at least one of manufacturing system 1702 or maintenance system 1704. In particular, control system 1714 may control the operation of at least one of fabrication equipment 1708, assembly equipment 1710, or maintenance equipment 1712.

The hardware in control system 1714 may be using hardware that may include computers, circuits, networks, and other types of equipment. Control system 1714 may perform direct control of manufacturing equipment 1706. For example, robots, computer controlled machines, and other equipment may be controlled by control system 1714. In other illustrative examples, control system 1714 may manage operations performed by human operators 1716 in manufacturing or performing maintenance on aircraft 1600 in FIG. 16. For example, control system 1714 may assign tasks, provide instructions, display models, or perform other operations to manage operations performed by human operators 1716. In these illustrative examples, at least one of analyzer 122 in FIG. 1 or rivet analyzer 202 in FIG. 2 may be implemented in control system 1714 to manage at least one of the manufacturing or maintenance of aircraft 1600 in FIG. 16. For example, control system 1714 may make changes in environmental factors, such as selecting different equipment installed rivets based on predicted concentricity for rivets not meeting specification limits as desired. In other words, some equipment may be more accurate than other equipment for installing rivets. As another example, control system 1714 may select different classes of rivets based on predicted concentricity of installed rivets in structures.

In the different illustrative examples, human operators 1716 may operate or interact with at least one of manufacturing equipment 1706, maintenance equipment 1712, or control system 1714. This interaction may be performed to manufacture aircraft 1600 in FIG. 16.

Of course, product management system 1700 may be configured to manage other products other than aircraft 1600 in FIG. 16. Although product management system 1700 has been described with respect to manufacturing in the aerospace industry, product management system 1700 may be configured to manage products for other industries. For example, product management system 1700 may be configured to manufacture products for the automotive industry as well as any other suitable industries.

Thus, one or more technical solutions are present that overcome a technical problem with obtaining measurements of desired parameters without using destructive testing. One or more technical solutions may provide a technical effect identifying destructive testing measurements without having to perform destructive testing. Also, one or more technical solutions are present that provide an ability to predict destructive testing measurement using statistical models.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component may be configured to perform the action or operation described. For example, the component may have a configuration or design for a structure that provides the component an ability to perform the action or operation that is described in the illustrative examples as being performed by the component.

Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A rivet measurement system for non-destructive testing measurements of production grade rivets for a production vehicle structure, the rivet measurement system comprising:
   a first measurement apparatus configured to acquire non-destructive testing measurements for sample production grade rivets of a particular class installed in the production vehicle structure, wherein the non-destructive testing measurements include a button height and a button diameter;
   a second measurement apparatus configured to acquire destructive testing measurements for the sample production grade rivets of the particular class, wherein the sample production grade rivets are drilled out and removed and the destructive testing measurements include a rivet button concentricity;
   a rivet analyzer configured to create a statistical model representing a relationship between the non-destructive testing measurements and the destructive testing measurements of the sample production grade rivets; and
   the rivet analyzer being further configured to:
      acquire the non-destructive testing measurements for the button height and the button diameter for additional production grade rivets of the particular class installed in the production vehicle structure;
      predict the rivet button concentricity for the additional production grade rivets from the non-destructive testing measurements for the button height and the button diameter using the statistical model; and
      determine whether the additional production grade rivets installed in the production vehicle structure are acceptable by comparing the rivet button concentricity predicted for the production rivets to specification limits for the particular class, to thereby enable a comparison of the non-destructive testing measurements of the additional production grade rivets to the specification limits without having to perform destructive testing.

2. The rivet measurement system of claim 1, wherein the rivet analyzer is configured to validate the statistical model by acquiring additional non-destructive testing measurements for additional sample production grade rivets of the particular class installed in the production vehicle structure, wherein the additional non-destructive testing measurements include a measure of the button height and the button diameter, acquiring additional destructive testing measurements for the additional sample production grade rivets, wherein the additional sample production grade rivets are drilled out and removed and the additional destructive testing measurements include the rivet button concentricity; predicting an additional rivet button concentricity for the additional sample production grade rivets from the button height and the button diameter measured in the additional non-destructive testing measurements and the statistical model; and comparing the additional rivet button concentricity predicted to the additional destructive testing measurements for the additional sample production grade rivets that include the rivet button concentricity to assess a predictive capability of the statistical model.

3. The rivet measurement system of claim 1, wherein the rivet analyzer generates an output indicating whether the non-destructive testing measurements of the sample production grade rivets installed on the production vehicle structure satisfy the specification limits.

4. The rivet measurement system of claim 1, wherein the rivet analyzer refines the statistical model through inclusion of additional destructive testing measurements and additional non-destructive testing measurements for additional sample of production grade rivets of the particular class installed in the production vehicle structure.

5. The rivet measurement system of claim 1, wherein in creating the statistical model, the rivet analyzer fits a linear expression representing the relationship between the non-destructive testing measurements and the destructive testing measurements of the sample production grade rivets results in the statistical model achieving a R-squared value of at least a predetermined acceptance threshold.

6. The rivet measurement system of claim 1, wherein the non-destructive testing measurements further include a rivet flushness.

7. The rivet measurement system of claim 1, wherein the statistical model employs a least-squares linear regression and is used to define a linear expression representing the relationship between the non-destructive testing measurements and the destructive testing measurements of the sample production grade rivets.

8. A method for non-destructive testing measurements of production rivets for a production vehicle structure, the method comprising:
   acquiring sample non-destructive testing measurements for sample production grade rivets of a particular class installed in the production vehicle structure for a production vehicle, wherein the non-destructive testing measurements include a button height and a button diameter;
   acquiring sample destructive testing measurements for the sample production grade rivets of the particular class, wherein the sample production grade rivets are drilled out and removed and the sample destructive testing measurements include a rivet button concentricity;
   creating a statistical model representing a relationship between the sample non-destructive testing measurements and the sample destructive testing measurements of the sample production grade rivets;
   acquiring non-destructive testing measurements for the button height and the button diameter for the sample production grade rivets of the particular class installed in the production vehicle structure;
   predicting the rivet button concentricity for the sample production grade rivets from the non-destructive testing measurements for the button height and the button diameter using the statistical model; and
   determining whether the sample production grade rivets installed in the production vehicle structure are acceptable by comparing the rivet button concentricity predicted for the sample production grade rivets to specification limits for the particular class, to thereby enable a comparison of the non-destructive testing measurements of the sample production grade rivets to the specification limits without having to perform destructive testing.

9. The method of claim 8 further comprising:
validating the statistical model by the steps of:
acquiring additional sample non-destructive testing measurements for additional sample production grade rivets of the particular class installed in the production vehicle structure, wherein the additional sample non-destructive testing measurements include a measure of the button height and the button diameter;
acquiring additional sample destructive testing measurements for the additional sample production grade rivets, wherein the additional sample production grade rivets are drilled out and removed and the additional sample destructive testing measurements include the rivet button concentricity;
predicting an additional rivet button concentricity for the additional sample production grade rivets from the button height and the button diameter measured and the statistical model; and
comparing the additional rivet button concentricity to the additional sample destructive testing measurements for the additional sample production grade rivets that include the rivet button concentricity to assess a predictive capability of the statistical model.

10. The method of claim 8 further comprising:
generating an output indicating whether the non-destructive testing measurements of the sample production grade rivets installed on the production vehicle structure satisfy the specification limits.

11. The method of claim 8 further comprising:
refining the statistical model through inclusion of additional sample destructive testing measurements and additional sample non-destructive testing measurements for additional sample production grade rivets of the particular class installed in the production vehicle structure.

12. The method of claim 8, wherein creating the statistical model comprises:
fitting a linear expression representing the relationship between the non-destructive testing measurements and the sample destructive testing measurements of the sample production grade rivets results in the statistical model achieving a R-squared value of at least a predetermined acceptance threshold.

13. The method of claim 8, wherein the non-destructive testing measurements further include a rivet flushness.

14. The method of claim 8, wherein the statistical model employs a least-squares linear regression and is used to define a linear expression representing the relationship between the non-destructive testing measurements and the sample destructive testing measurements of the sample production grade rivets.

15. A method for non-destructive testing of production grade fasteners, the method comprises:
acquiring non-destructive testing measurements for the production grade fasteners of a particular class installed in a production vehicle structure,
predicting destructive testing measurements for the production grade fasteners from the non-destructive testing measurements using a statistical model representing a relationship between the non-destructive testing measurements and the destructive testing measurements of the production grade fasteners; and
determining whether the production grade fasteners installed in the production vehicle structure are acceptable by comparing the destructive testing measurements predicted for the production grade fasteners to specification limits for the particular class, to thereby enable a comparison of the non-destructive testing measurements of additional production grade fasteners to the specification limits without having to perform destructive testing.

16. The method of claim 15 further comprising:
acquiring sample non-destructive testing measurements for sample production grade fasteners of the particular class installed in the production vehicle structure for a vehicle;
acquiring sample destructive testing measurements for the sample production grade fasteners of the particular class, wherein the sample production grade fasteners are removed for the sample destructive testing measurements; and
creating the statistical model representing the relationship between the sample non-destructive testing measurements and the sample destructive testing measurements of the sample production grade fasteners using the sample non-destructive testing measurements and the sample destructive testing measurements.

17. The method of claim 16 further comprising:
acquiring additional sample non-destructive testing measurements for additional sample production grade fasteners of the particular class installed in the production vehicle structure;
acquiring additional sample destructive testing measurements for the additional sample production grade fasteners, wherein the additional sample production grade fasteners are drilled out and removed;
determining predicted additional sample destructive testing measurements for the additional sample production grade fasteners from the additional sample non-destructive testing measurements and the statistical model; and
comparing predicted additional sample non-destructive testing measurements to the additional sample destructive testing measurements for the additional sample production grade fasteners to assess a predictive capability of the statistical model.

18. The method of claim 15, wherein the non-destructive testing measurements are selected from at least one of a button height, a button diameter, or a flushness.

19. The method of claim 15, wherein the destructive testing measurements are for at least one of a rivet button concentricity or a rivet interference.

20. The method of claim 15, wherein the production grade fasteners are selected from at least one of a rivet, a bolt, a screw, or a threaded fastener.

21. A fastener measurement system for non-destructive testing measurements of production grade fasteners for a production vehicle structure, the fastener measurement system comprising:
an analyzer configured to acquire the non-destructive testing measurements for the production grade fasteners of a particular class installed in the production vehicle structure, predict destructive testing measurements for the production grade fasteners from the non-destructive testing measurements using a statistical model representing a relationship between the non-destructive testing measurements and the destructive testing measurements of the production grade fasteners; and determine whether the production grade fasteners installed in the production vehicle structure are acceptable by comparing the destructive testing measurements predicted for the production grade fasteners to specification limits for the particular class, to thereby enable a comparison of the non-destructive testing measurements of additional production grade fasteners to the specification limits without having to perform destructive testing.

22. The fastener measurement system of claim 21, wherein the analyzer acquires sample non-destructive testing measurements for sample production grade fasteners of the particular class installed in the production vehicle structure for a vehicle, wherein the sample non-destructive testing measurements include a button height and a button diameter; acquires sample destructive testing measurements for the sample production grade fasteners of the particular class, wherein the sample production grade fasteners are removed for the destructive testing measurements; and creates the statistical model representing the relationship between the non-destructive testing measurements and destructive testing measurements of the production grade fasteners using the sample non-destructive testing measurements and the sample destructive testing measurements.

23. The fastener measurement system of claim 22, wherein the analyzer acquires additional sample non-destructive testing measurements for additional sample production grade fasteners of the particular class installed in the production vehicle structure; acquires additional sample destructive testing measurements for the additional sample production grade fasteners, wherein the additional sample production grade fasteners are drilled out and removed; determines predicted additional sample destructive testing measurements for the additional sample production grade fasteners from the additional sample non-destructive testing measurements and the statistical model; and compares predicted additional sample non-destructive testing measurements to the additional sample destructive testing measurements for the additional sample production grade fasteners to assess a predictive capability of the statistical model.

* * * * *